US011655494B2

(12) United States Patent
Knopfmacher et al.

(10) Patent No.: US 11,655,494 B2
(45) Date of Patent: May 23, 2023

(54) APPARATUS, SYSTEMS, AND METHODS FOR DETERMINING THE CONCENTRATION OF MICROORGANISMS AND THE SUSCEPTIBILITY OF MICROORGANISMS TO ANTI-INFECTIVES BASED ON REDOX REACTIONS

(71) Applicant: Avails Medical, Inc., Menlo Park, CA (US)

(72) Inventors: Oren S. Knopfmacher, San Francisco, CA (US); Meike Herget, Woodside, CA (US); Nitin K. Rajan, Palo Alto, CA (US); Michael D. Laufer, Menlo Park, CA (US)

(73) Assignee: Avails Medical, Inc., Menlo Park, CA (US)

( * ) Notice: Subject to any disclaimer, the term of this patent is extended or adjusted under 35 U.S.C. 154(b) by 69 days.

(21) Appl. No.: 16/814,153

(22) Filed: Mar. 10, 2020

(65) Prior Publication Data
US 2020/0224241 A1 Jul. 16, 2020

Related U.S. Application Data

(63) Continuation of application No. PCT/US2018/054003, filed on Oct. 2, 2018.

(60) Provisional application No. 62/567,648, filed on Oct. 3, 2017.

(51) Int. Cl.
*C12Q 1/18* (2006.01)
*C12Q 1/06* (2006.01)
*G01N 27/416* (2006.01)

(52) U.S. Cl.
CPC ............. *C12Q 1/18* (2013.01); *C12Q 1/06* (2013.01); *G01N 27/4168* (2013.01)

(58) Field of Classification Search
None
See application file for complete search history.

(56) References Cited

U.S. PATENT DOCUMENTS

| | | |
|---|---|---|
| 3,743,581 A | 7/1973 | Cady et al. |
| 4,200,493 A | 4/1980 | Wilkins et al. |
| 4,209,586 A | 6/1980 | Noller |
| 4,236,893 A | 12/1980 | Rice |
| 4,314,821 A | 2/1982 | Rice |
| 4,321,322 A * | 3/1982 | Ahnell ............... C12Q 1/04 205/777.5 |
| 4,448,534 A | 5/1984 | Wertz et al. |
| 4,615,978 A * | 10/1986 | Sandine ............. A23C 19/0323 426/34 |
| 4,735,906 A | 4/1988 | Bastiaans |
| 4,767,719 A | 8/1988 | Finlan |
| 4,789,804 A | 12/1988 | Karube et al. |
| 4,822,566 A | 4/1989 | Newman |
| 4,965,193 A | 10/1990 | Chen |
| 4,977,247 A | 12/1990 | Fahnestock et al. |
| 5,064,756 A | 11/1991 | Carr et al. |
| 5,077,210 A | 12/1991 | Eigler et al. |
| 5,111,221 A | 5/1992 | Fare et al. |
| 5,172,332 A | 12/1992 | Hungerford et al. |
| 5,182,005 A | 1/1993 | Schwiegk et al. |
| 5,218,304 A | 6/1993 | Kinlen et al. |
| 5,356,782 A | 11/1994 | Moorman et al. |
| 5,447,845 A | 9/1995 | Chu et al. |
| 5,821,399 A | 10/1998 | Zelin |
| 5,922,537 A | 7/1999 | Ewart et al. |
| 6,280,586 B1 | 8/2001 | Wolf et al. |
| 6,368,795 B1 | 4/2002 | Hefti |
| 6,391,558 B1 | 5/2002 | Henkens et al. |
| 6,391,577 B1 | 5/2002 | Mikkelsen et al. |
| 6,548,263 B1 | 4/2003 | Kapur et al. |
| 6,548,311 B1 | 4/2003 | Knoll |
| 6,780,307 B2 | 8/2004 | Kidwell |
| 6,863,792 B1 | 3/2005 | Madou et al. |
| 7,745,272 B2 | 6/2010 | Van De Walle et al. |
| 8,508,100 B2 | 8/2013 | Lee et al. |
| 8,728,844 B1 | 5/2014 | Liu et al. |

(Continued)

FOREIGN PATENT DOCUMENTS

| | | |
|---|---|---|
| CN | 101852765 A | 10/2010 |
| EP | 0235024 | 9/1987 |

(Continued)

OTHER PUBLICATIONS

Wan et al., 2011 (Impedimetric immunosensor doped with reduced graphene sheets fabricated by controllable electrodeposition for the non-labelled detection of bacteria; Biosensors and Bioelectronics 26 (2011) 1959-1964). (Year: 2011).*

Berney et al. "A DNA diagnostic biosensor: development, characterization and performance" Sensors and Actuators B: Chemical: International Journal Devoted to Research and Development of Physical and Chemical Transducers, Elsevier BV, NL, vol. 68, No. 1-3, Aug. 25, 2000, pp. 100-108.

Dortet, Laurent et al., "Bloodstream Infections Caused by *Pseudomonas* spp.: How To Detect Carbapenemase Producers Directly from Blood Cultures", Journal of Clinical Microbiology, 52(4):1269-1273, Apr. 2014.

Dortet, Laurent et al., "CarbAcineto NP Test for Rapid Detection of Carbapenemase-Producing *Acinetobacter* spp.", Journal of Clinical Microbiology, 52(7):2359-2364, Jul. 2014.

(Continued)

*Primary Examiner* — Mary Maille Lyons
(74) *Attorney, Agent, or Firm* — Levine Bagade Han LLP

(57) ABSTRACT

Various methods, devices, and systems for determining the concentration of microorganisms in a sample and determining the susceptibility of such microorganisms to one or more antibiotics or other types of anti-infectives are disclosed herein. More specifically, methods for quantifying microorganisms based on redox reactions are disclosed along with systems and devices for quantifying such microorganisms using certain oxidation reduction potential (ORP) sensors. Moreover, methods for determining the susceptibility and the degree of susceptibility of microorganisms to one or more anti-infectives are disclosed along with multiplex systems for such assays.

14 Claims, 9 Drawing Sheets

(56) References Cited

U.S. PATENT DOCUMENTS

| | | |
|---|---|---|
| 9,377,456 B1 | 6/2016 | Herget et al. |
| 9,702,847 B2 | 7/2017 | Herget et al. |
| 9,766,201 B2 | 9/2017 | Herget et al. |
| 9,944,969 B2 | 4/2018 | Knopfmacher et al. |
| 9,963,733 B2 | 5/2018 | Knopfmacher et al. |
| 10,060,916 B2 | 8/2018 | Knopfmacher |
| 10,174,356 B2 | 1/2019 | Knopfmacher et al. |
| 10,254,245 B2 | 4/2019 | Knopfmacher et al. |
| 11,385,200 B2 | 7/2022 | Knopfmacher et al. |
| 2002/0127623 A1 | 9/2002 | Minshull et al. |
| 2003/0073071 A1 | 4/2003 | Fritz et al. |
| 2003/0109056 A1 | 6/2003 | Vossmeyer et al. |
| 2003/0119208 A1 | 6/2003 | Yoon et al. |
| 2004/0195098 A1 | 10/2004 | Ley et al. |
| 2005/0116263 A1 | 6/2005 | Lu et al. |
| 2006/0088839 A1 | 4/2006 | Matsui et al. |
| 2006/0102935 A1 | 5/2006 | Yitzchaik et al. |
| 2006/0197118 A1 | 9/2006 | Migliorato et al. |
| 2006/0246426 A1 | 11/2006 | Woodbury et al. |
| 2006/0286548 A1 | 12/2006 | Liposky |
| 2007/0037225 A1 | 2/2007 | Metzger et al. |
| 2007/0054396 A1 | 3/2007 | Peppers et al. |
| 2007/0072187 A1 | 3/2007 | Blok et al. |
| 2008/0012007 A1 | 1/2008 | Li et al. |
| 2008/0199863 A1 | 8/2008 | Haake et al. |
| 2009/0008247 A1 | 1/2009 | Chen et al. |
| 2009/0020438 A1 | 1/2009 | Hodges |
| 2009/0273354 A1 | 11/2009 | Dhirani et al. |
| 2010/0025660 A1 | 2/2010 | Jain et al. |
| 2010/0137143 A1 | 6/2010 | Rothberg et al. |
| 2010/0194409 A1 | 8/2010 | Gao et al. |
| 2011/0068372 A1 | 3/2011 | Ren et al. |
| 2011/0306032 A1 | 12/2011 | Galiano et al. |
| 2012/0032235 A1 | 2/2012 | Bikumandla |
| 2012/0077692 A1 | 3/2012 | Hassibi et al. |
| 2012/0088682 A1 | 4/2012 | Rothberg et al. |
| 2012/0143027 A1 | 6/2012 | Phillips et al. |
| 2012/0153262 A1 | 6/2012 | Paranjape et al. |
| 2012/0153407 A1 | 6/2012 | Chang et al. |
| 2012/0165246 A1 | 6/2012 | Lindner et al. |
| 2012/0168306 A1 | 7/2012 | Hassibi et al. |
| 2012/0208291 A1 | 8/2012 | Davis et al. |
| 2012/0214172 A1 | 8/2012 | Chen et al. |
| 2012/0261274 A1 | 10/2012 | Rearick et al. |
| 2012/0256166 A1 | 11/2012 | Chen et al. |
| 2012/0279859 A1 | 11/2012 | Rothberg et al. |
| 2013/0089883 A1 | 4/2013 | Dallenne et al. |
| 2013/0089932 A1 | 4/2013 | Wu et al. |
| 2013/0096013 A1 | 4/2013 | Esfandyarpour et al. |
| 2013/0105868 A1 | 5/2013 | Kalnitsky et al. |
| 2013/0217063 A1 | 8/2013 | Metzger et al. |
| 2014/0011218 A1 | 1/2014 | Han et al. |
| 2014/0057339 A1 | 2/2014 | Esfandyarpour et al. |
| 2014/0134656 A1 | 5/2014 | Dortet et al. |
| 2014/0186215 A1 | 6/2014 | Shinta et al. |
| 2014/0191294 A1 | 7/2014 | Bikumandla et al. |
| 2014/0231256 A1 | 8/2014 | Packingham et al. |
| 2014/0349005 A1 | 11/2014 | Everett et al. |
| 2015/0355129 A1 | 12/2015 | Knopfmacher |
| 2016/0039657 A1 | 2/2016 | Jain et al. |
| 2016/0068417 A1 | 3/2016 | Buschmann |
| 2016/0187332 A1 | 6/2016 | Herget et al. |
| 2016/0187334 A1 | 6/2016 | Herget et al. |
| 2016/0208306 A1 | 7/2016 | Pollak et al. |
| 2016/0209356 A1 | 7/2016 | Herget et al. |
| 2016/0266102 A1 | 9/2016 | Knopfmacher |
| 2016/0369318 A1 | 12/2016 | Carlisle et al. |
| 2017/0058313 A1 | 3/2017 | Knopfmacher et al. |
| 2017/0059508 A1 | 3/2017 | Knopfmacher et al. |
| 2017/0212075 A1 | 7/2017 | Knopfmacher et al. |
| 2017/0336348 A1 | 11/2017 | Herget et al. |
| 2017/0342459 A1 | 11/2017 | Knopfmacher et al. |
| 2018/0195106 A1 | 7/2018 | Knopfmacher et al. |
| 2018/0364221 A1 | 12/2018 | Knopfmacher |
| 2019/0046984 A1 | 2/2019 | Kelley et al. |
| 2019/0136290 A1 | 5/2019 | Knopfmacher et al. |
| 2019/0293529 A1 | 9/2019 | Rajan et al. |
| 2019/0310214 A1 | 10/2019 | Herget et al. |
| 2020/0150082 A1 | 5/2020 | Knopfmacher et al. |
| 2021/0325371 A1 | 10/2021 | Rajan et al. |

FOREIGN PATENT DOCUMENTS

| | | |
|---|---|---|
| EP | 1460130 | 9/2004 |
| EP | 2172767 | 4/2010 |
| JP | 1988-066454 | 3/1988 |
| JP | 1996-0886771 | 4/1996 |
| JP | 2006-511818 | 4/2006 |
| JP | 2011-58900 | 3/2011 |
| JP | 2011-085038 | 11/2012 |
| WO | WO 1992/009700 | 6/1992 |
| WO | WO 2003/044530 | 5/2003 |
| WO | WO 2003/052097 | 6/2003 |
| WO | WO 2004/077052 | 9/2004 |
| WO | WO 2006/102695 | 10/2006 |
| WO | WO 2007/035814 | 3/2007 |
| WO | WO 2009/021908 | 2/2009 |
| WO | WO 2010/062001 | 6/2010 |
| WO | WO 2012/078340 | 6/2012 |
| WO | WO 2013/096404 | 6/2013 |
| WO | WO 2014/080292 | 5/2014 |
| WO | WO 2014/134431 | 9/2014 |
| WO | WO 2015/077632 | 5/2015 |
| WO | WO 2015/188002 | 12/2015 |
| WO | WO 2016/005743 | 1/2016 |
| WO | WO 2016/028233 | 2/2016 |
| WO | WO 2016/044417 | 3/2016 |
| WO | WO 2016/061453 | 4/2016 |
| WO | WO 2016/065475 | 5/2016 |
| WO | WO 2016/109569 | 7/2016 |
| WO | WO 2017/035393 | 3/2017 |
| WO | WO 2017/107333 | 6/2017 |
| WO | WO 2017/132095 | 8/2017 |
| WO | WO 2017/209839 | 12/2017 |
| WO | WO 2018/111234 | 6/2018 |
| WO | WO 2018/145338 | 8/2018 |
| WO | WO 2019/005296 | 1/2019 |
| WO | WO 2019/070739 | 4/2019 |
| WO | WO 2019/113226 | 6/2019 |
| WO | WO 2019/246208 | 12/2019 |
| WO | WO 2020/117650 | 6/2020 |

OTHER PUBLICATIONS

Dortet, Laurent et al., "Evaluation of the RAPIDECw Carba NP, the Rapid CARB Screenw and the Carba NP test for biochemical detection of carbapenemase-producing Enterobacteriaceae", J Antimicrob Chemother, 70:3014-3022, 2015.

Dortet, Laurent et al., "Further Proofs of Concept for the Carba NP Test", Antimicrobial Agents and Chemotherapy, 58(2):1269, Feb. 2014.

Dortet, Laurent et al., "Rapid Identification of Carbapenemase Types in Enterobacteriaceae and *Pseudomonas* spp. by Using a Biochemical Test", Antimicrobial Agents and Chemotherapy, 56(12):6437-6440, Dec. 2012.

Estrela, Pedro et al., "Label-Free Sub-picomolar Protein Detection with Field-Effect Transistors," Analytical Chemistry, vol. 82, No. 9, May 1, 2010, 3531-3536.

Hammock, Mallory L. et al., "Electronic readout ELISA with organic field-effect transistors as a prognostic test for preeclampsia," Advanced Materials, 26: 6138-6144. doi: 10.1002/adma. 201401829.

Kumar et al., "Sensitivity Enhancement Mechanisms in Textured Dielectric Based Electrolyte-Insulator-Semiconductor (EIS) Sensors," *ECS Journal of Solid State Science and Technology*, 4(3):N18-N23 (2015).

Mathias, W. et al., "Selective Sodium Sensing with Gold-Coated Silicon Nanowire Field-Effect Transistors in a Differential Setup," ACS Nano 7, 5978-5983 (2013).

Nordmann, Patrice et al., "Strategies for identification of carbapenemase-producing Enterobacteriaceae", J Antimicrob Chemother, 68:487-489, 2013.

(56) References Cited

OTHER PUBLICATIONS

Oliu et al., "Impedimetric Sensors for Bacteria Detection," Biosensors—Micro and Nanoscale Applications, Chpt. 9 (Sep. 2015) p. 257-288.
Poghossian et al., "Penicillin Detection by Means of Field-Effect Based Sensors: EnFET, Capacitive EIS Sensor or LAPS?", *Sensors and Actuators B*, 78:237 (2001).
Poirel, Laurent et al., "Rapidec Carba NP Test for Rapid Detection of Carbapenemase Producers", Journal of Clinical Microbiology, 53(9):3003-3008, Sep. 2015.
Pourciel-Gouzy M L et al: "pH-ChemFET-based analysis devices for the bacterial activity monitoring." Sensors and Actuators B: Chemical: International Journal Devoted to Research and Development of Physical and Chemical Transducers, Elsevier BV, NL, vol. 134, No. 1, Aug. 28, 2008, pp. 339-344.
Salm, Eric et al., "Electrical Detection of Nucleic Acid Amplification Using an On-Chip Quasi-Reference Electrode and a PVC REFET," dx.doi.org/10.1021/ac500897t, *Anal. Chem.*, 2014, 86, 6968-6975.
Schoning, Michael J., "'Playing Around' with Field-Effect Sensors on the Basis of EIS Structures, LAPS and ISFETs," *Sensors*, 5:126-138 (2005).
Grossi Marco et al. "Bacterial concentration detection using a portable embedded sensor system for environmental monitoring", 2017 7th IEE International Workshop on Advances in Senors and Interfaces (IWASI), IEEE, Jun. 15, 2017, pp. 246-251.
Ivnitsky D et al.: "Biosensors for Detection of Pathogenic Bacteria", Biosensors and Bioelectronics, Elsevier Science Ltd. UK, Amsterdam, NL, vol. 14, No. 7, Oct. 1, 1999, pp. 599-624.
J. Parce et al: "Detection of cell-affecting agents with a silicon biosensor", Science, vol. 246, No. 4927, Oct. 13, 1989 (Oct. 13, 1989), pp. 243-247.
Yu Allen C et al: Moni tori ng bacterial growth using tunable resistive pulse sensing with a pore-based technique11 , Applied Microbiology and Biotechnology, Springer Berlin Heidelberg, Berlin/Heidelberg, vol. 98, No. 2, Nov. 29, 2013, pp. 855-862.
Zhang, Xuzhi et al.: Online Monitoring of Bacterial Growth with an Electrical Sensor11 , Analytical Chemistry, vol. 90, No. 10, Apr. 24, 2018 (Apr. 24, 2018), pp. 6006-6011.
Zhou, Yong-Jun et al.: Real-time Detection System for Amount of Bacteria Based on an Electrochemical Sensor, Instrument Technique and Sensor, vol. 2, No. 2, Feb. 28, 2014 (Feb. 28, 2014), pp. 71-72 and 86.
Dutton 1978 (Redox potentiometry: Determination of midpoint potentials of oxidation-reduction components of biological electron-transfer systems; In Methods in Enzymology, 54:411-435) (Year: 1978).
Kang et al. "Survey of Redox-Active Moieties for Application in Multiplexed Electrochemical Biosensors", Anal. Chem., vol. 88, pp. 10452-10458, 2016.
Zuhri et al. 2016 (Effect of Methylene Blue Addition as a Redox Mediator on Performance of Microbial Desalination Cell by Utilizing Tempe Wastewater; International Journal of Technology 6: 952-961). (Year: 2016).
Kazuo Iwata, Akira Matsuda, Effect of Mixed Culture of Redox Potentials of Candida and Various Bacteria, Sep. 1962, Fungus and Fungus Disease, vol. 3, No. 2, pp. 56-60.

* cited by examiner

APPARATUS, SYSTEMS, AND METHODS FOR DETERMINING THE CONCENTRATION OF MICROORGANISMS AND THE SUSCEPTIBILITY OF MICROORGANISMS TO ANTI-INFECTIVES BASED ON REDOX REACTIONS

CROSS-REFERENCE TO RELATED APPLICATIONS

This application is a continuation of PCT Application No. PCT/US2018/054003 filed on Oct. 2, 2018, which claims the benefit of U.S. Provisional Application No. 62/567,648 filed on Oct. 3, 2017, the contents of which are incorporated herein by reference in their entities.

TECHNICAL FIELD

The present disclosure relates generally to in vitro detection of microorganisms or infectious agents and, more specifically, to apparatus, systems, and methods for determining the concentration of microorganisms or infectious agents and the susceptibility of such microorganisms or infectious agents to anti-infectives.

BACKGROUND

Infections caused by anti-infective resistant microorganisms or infectious agents are a significant problem for healthcare professionals in hospitals, nursing homes, and other healthcare environments. Rapid detection of such microorganisms is crucial in order to prevent the spread of their resistance profiles. When faced with such an infection, a preferred course of action is for a clinician to use anti-infective compounds judiciously, preferably only those necessary to alleviate the infection. However, what occurs most frequently today is that broad spectrum anti-infectives are given to the patient to ensure adequacy of treatment. This tends to result in microorganisms with multiple anti-infective resistances. Ideally, the sensitivity of the microorganism to anti-infectives would be detected soon after its presence is identified.

Existing methods and instruments used to detect anti-infective resistance in microorganisms include costly and labor intensive microbial culturing techniques to isolate the microorganism and include tests such as agar disk diffusion or broth microdilution where anti-infectives are introduced as liquid suspensions, paper disks, or dried gradients on agar media. However, those methods require manual interpretation by skilled personnel and are prone to technical or clinician error.

While automated inspection of such panels or media can reduce the likelihood of clinician error, current instruments used to conduct these inspections are often complex and require the addition of reporter molecules or use of costly components such as transparent indium tin oxide (ITO) electrodes. In addition, current instruments often rely on an optical read-out of the investigated samples, which require bulky detection equipment.

As a result of the above limitations and restrictions, there is a need for improved apparatus, systems, and methods to quickly and effectively detect anti-infective resistant microorganisms in a patient sample.

SUMMARY

Various apparatus, systems and methods for detecting the susceptibility of an infectious agent in a sample to one or more anti-infectives are described herein. In one embodiment a method of determining a concentration of an infectious agent can involve diluting a sample comprising the infectious agent with a dilutive solution to yield a diluted sample. The method can further involve introducing the diluted sample to a sensor such that the diluted sample is in fluid communication with a redox-active material of the sensor. The method can also involve monitoring an oxidation reduction potential (ORP) of the diluted sample over a period of time using at least one parameter analyzer coupled to the sensor to determine the concentration of the infectious agent in the sample. The ORP can be monitored in the absence of any added reporter molecules in the diluted sample.

In another embodiment, a system to determine a concentration of an infectious agent is disclosed comprising a metering conduit configured to deliver a dilutive solution to a sample comprising the infectious agent to yield a diluted sample. The system can comprise a redox-active material, a sample delivery conduit configured to introduce the diluted sample to the sensor, and at least one parameter analyzers coupled to the sensor. The parameter analyzer can be configured to monitor an ORP of the diluted sample over a period of time when the diluted sample is in fluid communication with the redox-active material of the sensor. The ORP can be monitored in the absence of any added reporter molecules in the diluted sample to determine the concentration of the infectious agent in the sample.

In another embodiment, a method of determining a susceptibility of an infectious agent to an anti-infective can involve diluting a sample comprising the infectious agent with a dilutive solution to yield a diluted sample. The method can also involve separating the diluted sample into a first aliquot and a second aliquot. The second aliquot can be used as a control solution. The method can also involve mixing an anti-infective at a first concentration into the first aliquot to yield a test solution and introducing the test solution to a first sensor such that the test solution is in fluid communication with a redox-active material of the first sensor. The method can further involve introducing the control solution to a second sensor such that the control solution is in fluid communication with the redox-active material of the second sensor. The method can also involve monitoring an ORP of the test solution and the control solution over a period of time using one or more parameter analyzers coupled to the first sensor, the second sensor, or a combination thereof. The ORPs can be monitored in the absence of any added reporter molecules in the test solution or the control solution. The method can further involve comparing the ORP of the test solution with the ORP of the control solution to determine the susceptibility of the infectious agent to the anti-infective.

In yet another embodiment, a system to determine a susceptibility of an infectious agent to one or more anti-infectives can comprise a metering conduit configured to deliver a dilutive solution to a sample comprising the infectious agent to yield a diluted sample. The metering conduit can separate the diluted sample into a first aliquot and a second aliquot. The second aliquot can be used as a control solution. The system can also comprise a first sensor comprising a redox-active material and a second sensor comprising the redox-active material.

The system can also comprise a first sample delivery conduit configured to introduce the first aliquot to the first sensor. The first sample delivery conduit can comprise a first anti-infective at a first concentration. The first aliquot can mix with the first anti-infective to form a first test solution.

The system can also comprise a second sample delivery conduit configured to introduce the control solution to the second sensor.

The system can further comprise one or more parameter analyzers coupled to the first sensor and the second sensor. The one or more parameter analyzers can monitor an ORP of the first test solution over a period of time when the first test solution is in fluid communication with the redox-active material of the first sensor. The ORP can be monitored in the absence of any added reporter molecules in the first test solution. The one or more parameter analyzers can also monitor the ORP of the control solution over a period of time when the control solution is in fluid communication with the redox-active material of the second sensor. The ORP can be monitored in the absence of any added reporter molecules in the control solution. The one or more parameter analyzers or another device within the system can compare the ORP of the first test solution with the ORP of the control solution to determine the susceptibility of the infectious agent to the first anti-infective.

DETAILED DESCRIPTION

Variations of the devices, systems, and methods described herein are best understood from the detailed description when read in conjunction with the accompanying drawings. It is emphasized that, according to common practice, the various features of the drawings may not be to scale. On the contrary, the dimensions of the various features may be arbitrarily expanded or reduced for clarity and not all features may be visible or labeled in every drawing. The drawings are taken for illustrative purposes only and are not intended to define or limit the scope of the claims to that which is shown.

Figure 1:
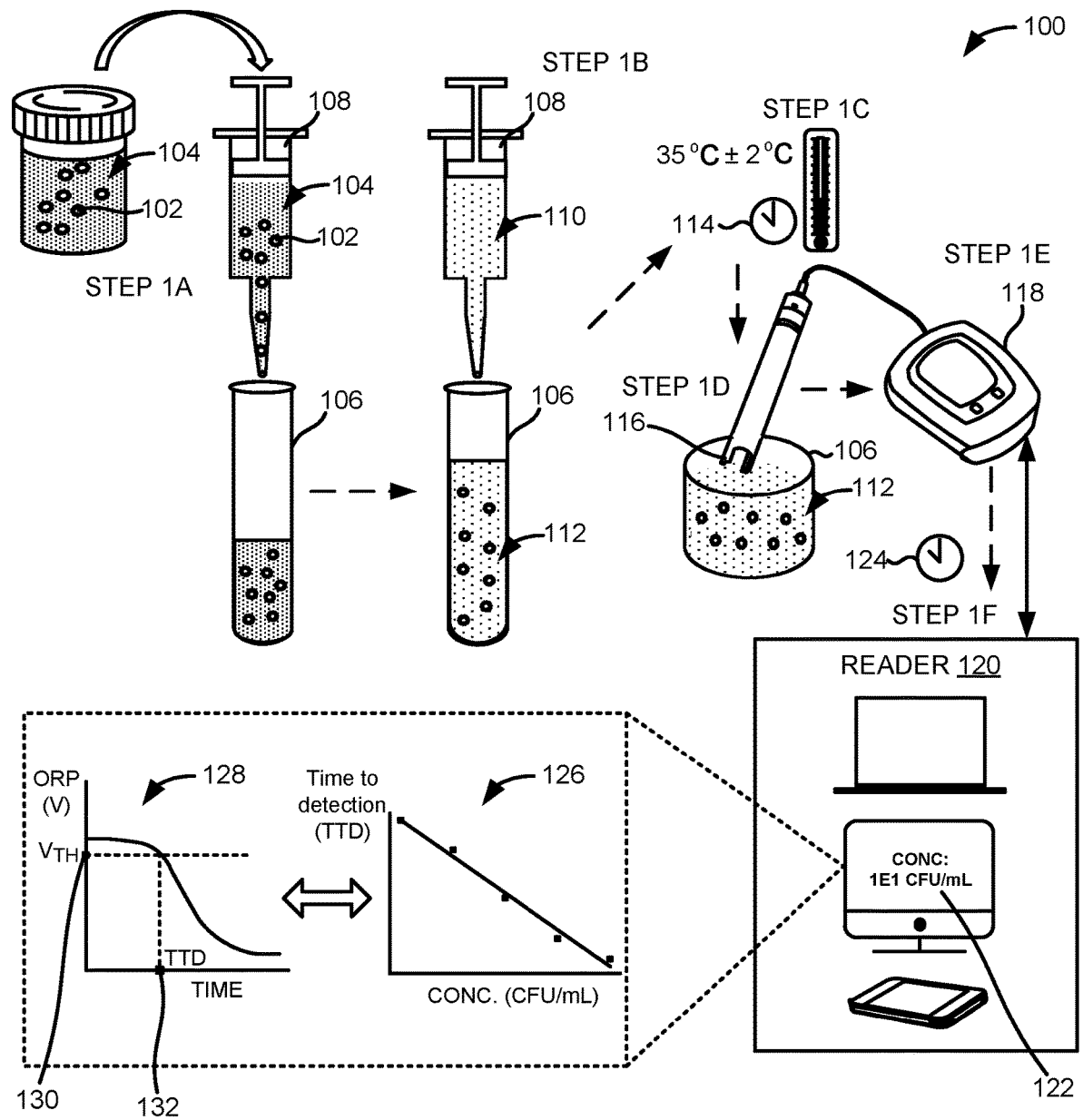
FIG. 1 illustrates one embodiment of a method for determining the concentration of one or more infectious agents in a biological sample.

FIG. 1 illustrates an embodiment of a method 100 for determining the concentration of one or more infectious agents 102 in a sample 104. The method 100 can comprise introducing one or more aliquots of the sample 104 into one or more reaction vessels 106 in step 1A. The reaction vessels 106 can refer to one or more test tubes, reaction tubes, wells of a high throughput assay plate or well plate such as a 96-well plate, a 192-well plate, or a 384-well plate, culture plates or dishes, or other suitable containers for housing biological samples. One or more fluid delivery conduits 108 can inject, deliver, or otherwise introduce the aliquots of the sample 104 to the one or more reaction vessels 106.

In other embodiments not shown in FIG. 1, a stimulus solution can be added to the sample 104 before introducing the sample 104 to the reaction vessel 106. The stimulus solution can be a nutrient or growth solution. In these and other embodiments, the sample 104 can also be filtered before step 1A. This filtering step can involve filtering the sample 104 using an instance of a filter, a microfluidic filter, or a combination thereof to filter out debris, inorganic material, and larger cellular components including blood cells or epithelial cells from the sample 104.

The sample 104 can comprise at least one of a biological sample, a bodily fluid, a wound swab or sample, a rectal swab or sample, and a bacterial culture derived from the biological sample, the bodily fluid, the wound swab or sample, or the rectal swab or sample. The bodily fluid can comprise urine, blood, serum, plasma, saliva, sputum, semen, breast milk, joint fluid, spinal fluid, wound material, mucus, fluid accompanying stool, re-suspended rectal or wound swabs, vaginal secretions, cerebrospinal fluid, synovial fluid, pleural fluid, peritoneal fluid, pericardial fluid, amniotic fluid, cultures of bodily which has been tested positive for bacteria or bacterial growth such as blood culture which has been tested positive for bacteria or bacterial growth (i.e., positive blood culture), or a combination thereof.

The infectious agents 102 that can be quantified using the methods or systems disclosed herein can be any metabolizing single- or multi-cellular organism including bacteria and fungi. In certain embodiments, the infectious agent 102 can be bacteria selected from the genera *Acinetobacter, Acetobacter, Actinomyces, Aerococcus, Aeromonas, Agrobacterium, Anaplasma, Azorhizobium, Azotobacter, Bacillus, Bacteroides, Bartonella, Bordetella, Borrelia, Brucella, Burkholderia, Calymmatobacterium, Campylobacter, Chlamydia, Chlamydophila, Citrobacter, Clostridium, Corynebacterium, Coxiella, Ehrlichia, Enterobacter, Enterococcus, Escherichia, Francisella, Fusobacterium, Gardnerella, Haemophilus, Helicobacter, Klebsiella, Lactobacillus, Legionella, Listeria, Methanobacterium, Microbacterium, Micrococcus, Morganella, Moraxella, Mycobacterium, Mycoplasma, Neisseria, Pandoraea, Pasteurella, Peptostreptococcus, Porphyromonas, Prevotella, Proteus, Providencia, Pseudomonas, Ralstonia, Raoultella, Rhizobium, Rickettsia, Rochalimaea, Rothia, Salmonella, Serratia, Shewanella, Shigella, Spirillum, Staphylococcus, Strenotrophomonas, Streptococcus, Streptomyces, Treponema, Vibrio, Wolbachia, Yersinia*, or a combination thereof. In other embodiments, the infectious agent 102 can be one or more fungi selected from the genera *Candida* or *Cryptococcus* or mold.

Other specific bacteria that can be quantified using the methods and systems disclosed herein can comprise *Staphy-* lococcus aureus, Staphylococcus lugdunensis*, coagulase-negative *Staphylococcus* species (including but not limited to *Staphylococcus epidermidis, Staphylococcus haemolyticus, Staphylococcus hominis, Staphylococcus capitis*, not differentiated), *Enterococcus faecalis, Enterococcus faecium* (including but not limited to *Enterococcus faecium* and other *Enterococcus* spp., not differentiated, excluding *Enterococcus faecalis*), *Streptococcus pneumoniae, Streptococcus pyogenes, Streptococcus agalactiae, Streptococcus* spp., (including but not limited to *Streptococcus mitis, Streptococcus pyogenes, Streptococcus gallolyticus, Streptococcus agalactiae, Streptococcus pneumoniae*, not differentiated), *Pseudomonas aeruginosa, Acinetobacter baumannii, Klebsiella* spp. (including but not limited to *Klebsiella pneumoniae, Klebsiella oxytoca*, not differentiated), *Escherichia coli, Enterobacter* spp. (including but not limited to *Enterobacter cloacae, Enterobacter aerogenes*, not differentiated), *Proteus* spp. (including but not limited to *Proteus mirabilis, Proteus vulgaris*, not differentiated), *Citrobacter* spp. (including but not limited to *Citrobacter freundii, Citrobacter koseri*, not differentiated), *Serratia marcescens, Candida albicans*, and *Candida glabrata*.

Other more specific bacteria that can be quantified can comprise *Acinetobacter baumannii, Actinobacillus* spp., *Actinomycetes, Actinomyces* spp. (including but not limited to *Actinomyces israelii* and *Actinomyces naeslundii*), *Aeromonas* spp. (including but not limited to *Aeromonas hydrophila, Aeromonas veronii* biovar *sobria* (*Aeromonas sobria*), and *Aeromonas caviae*), *Anaplasma phagocytophilum, Alcaligenes xylosoxidans, Actinobacillus actinomycetemcomitans, Bacillus* spp. (including but not limited to *Bacillus anthracis, Bacillus cereus, Bacillus subtilis, Bacillus thuringiensis*, and *Bacillus stearothermophilus*), *Bacteroides* spp. (including but not limited to *Bacteroides fragilis*), *Bartonella* spp. (including but not limited to *Bartonella bacilliformis* and *Bartonella henselae*), *Bifidobacterium* spp., *Bordetella* spp. (including but not limited to *Bordetella pertussis, Bordetella parapertussis*, and *Bordetella bronchiseptica*), *Borrelia* spp. (including but not limited to *Borrelia recurrentis*, and *Borrelia burgdorferi*), *Brucella* sp. (including but not limited to *Brucella abortus, Brucella canis, Brucella melintensis* and *Brucella suis*), *Burkholderia* spp. (including but not limited to *Burkholderia pseudomallei* and *Burkholderia cepacia*), *Campylobacter* spp. (including but not limited to *Campylobacter jejuni, Campylobacter coli, Campylobacter lari* and *Campylobacter fetus*), *Capnocytophaga* spp., *Cardiobacterium hominis, Chlamydia trachomatis, Chlamydophila pneumoniae, Chlamydophila psittaci, Citrobacter* spp. *Coxiella burnetii, Corynebacterium* spp. (including but not limited to, *Corynebacterium diphtheriae, Corynebacterium jeikeum* and *Corynebacterium*), *Clostridium* spp. (including but not limited to *Clostridium perfringens, Clostridium difficile, Clostridium botulinum* and *Clostridium tetani*), *Eikenella corrodens, Enterobacter* spp. (including but not limited to *Enterobacter aerogenes, Enterobacter agglomerans, Enterobacter cloacae* and *Escherichia coli*, including opportunistic *Escherichia coli*, including but not limited to enterotoxigenic *E. coli*, enteroinvasive *E. coli*, enteropathogenic *E. coli*, enterohemorrhagic *E. coli*, enteroaggregative *E. coli* and uropathogenic *E. coli*) *Enterococcus* spp. (including but not limited to *Enterococcus faecalis* and *Enterococcus faecium*) *Ehrlichia* spp. (including but not limited to *Ehrlichia chafeensia* and *Ehrlichia canis*), *Erysipelothrix rhusiopathiae, Eubacterium* spp., *Francisella tularensis, Fusobacterium nucleatum, Gardnerella vaginalis, Gemella morbillorum, Haemophilus* spp. (including but not limited to *Haemophilus influenzae, Haemophilus ducreyi, Haemophilus aegyptius, Haemophilus parainfluenzae, Haemophilus haemolyticus* and *Haemophilus parahaemolyticus, Helicobacter* spp. (including but not limited to *Helicobacter pylori, Helicobacter cinaedi* and *Helicobacter fennelliae*), *Kingella kingii, Klebsiella* spp. (including but not limited to *Klebsiella pneumoniae, Klebsiella granulomatis* and *Klebsiella oxytoca*), *Lactobacillus* spp., *Listeria monocytogenes, Leptospira interrogans, Legionella pneumophila, Leptospira interrogans, Peptostreptococcus* spp., *Moraxella catarrhalis, Morganella* spp., *Mobiluncus* spp., *Micrococcus* spp., *Mycobacterium* spp. (including but not limited to *Mycobacterium leprae, Mycobacterium tuberculosis, Mycobacterium intracellulare, Mycobacterium avium, Mycobacterium bovis*, and *Mycobacterium marinum*), *Mycoplasm* spp. (including but not limited to *Mycoplasma pneumoniae, Mycoplasma hominis*, and *Mycoplasma genitalium*), *Nocardia* spp. (including but not limited to *Nocardia asteroides, Nocardia cyriacigeorgica* and *Nocardia brasiliensis*), *Neisseria* spp. (including but not limited to *Neisseria gonorrhoeae* and *Neisseria meningitidis*), *Pasteurella multocida, Plesiomonas shigelloides. Prevotella* spp., *Porphyromonas* spp., *Prevotella melaninogenica, Proteus* spp. (including but not limited to *Proteus vulgaris* and *Proteus mirabilis*), *Providencia* spp. (including but not limited to *Providencia alcalifaciens, Providencia rettgeri* and *Providencia stuartii*), *Pseudomonas aeruginosa, Propionibacterium acnes, Rhodococcus equi, Rickettsia* spp. (including but not limited to *Rickettsia rickettsii, Rickettsia akari* and *Rickettsia prowazekii, Orientia tsutsugamushi* (formerly: *Rickettsia tsutsugamushi*) and *Rickettsia typhi*), *Rhodococcus* spp., *Serratia marcescens, Stenotrophomonas maltophilia, Salmonella* spp. (including but not limited to *Salmonella enterica, Salmonella typhi, Salmonella paratyphi, Salmonella enteritidis, Salmonella cholerasuis* and *Salmonella typhimurium*), *Serratia* spp. (including but not limited to *Serratia marcesans* and *Serratia liquifaciens*), *Shigella* spp. (including but not limited to *Shigella dysenteriae, Shigella flexneri, Shigella boydii* and *Shigella sonnei*), *Staphylococcus* spp. (including but not limited to *Staphylococcus aureus, Staphylococcus epidermidis, Staphylococcus hemolyticus, Staphylococcus saprophyticus*), *Streptococcus* spp. (including but not limited to *Streptococcus pneumoniae* (for example chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, erythromycin-resistant serotype 14 *Streptococcus pneumoniae*, optochin-resistant serotype 14 *Streptococcus pneumoniae*, rifampicin-resistant serotype 18C *Streptococcus pneumoniae*, tetracycline-resistant serotype 19F *Streptococcus pneumoniae*, penicillin-resistant serotype 19F *Streptococcus pneumoniae*, and trimethoprim-resistant serotype 23F *Streptococcus pneumoniae*, chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, optochin-resistant serotype 14 *Streptococcus pneumoniae*, rifampicin-resistant serotype 18C *Streptococcus pneumoniae*, penicillin-resistant serotype 19F *Streptococcus pneumoniae*, or trimethoprim-resistant serotype 23F *Streptococcus pneumoniae*), *Streptococcus agalactiae, Streptococcus mutans, Streptococcus pyogenes*, Group A streptococci, *Streptococcus pyogenes*, Group B streptococci, *Streptococcus agalactiae*, Group C streptococci, *Streptococcus anginosus, Streptococcus equismilis*, Group D streptococci, *Streptococcus bovis*, Group F streptococci, and *Streptococcus anginosus* Group G streptococci), *Spirillum minus, Streptobacillus moniliformi,*

*Treponema* spp. (including but not limited to *Treponema carateum, Treponema petenue, Treponema pallidum* and *Treponema endemicum, Tropheryma whippelii, Ureaplasma urealyticum, Veillonella* sp., *Vibrio* spp. (including but not limited to *Vibrio cholerae, Vibrio parahemolyticus, Vibrio vulnificus, Vibrio parahaemolyticus, Vibrio vulnificus, Vibrio alginolyticus, Vibrio mimicus, Vibrio hollisae, Vibrio fluvialis, Vibrio metchnikovii, Vibrio damsela* and *Vibrio furnisii*), *Yersinia* spp. (including but not limited to *Yersinia enterocolitica, Yersinia pestis,* and *Yersinia pseudotuberculosis*) and *Xanthomonas maltophilia* among others.

Furthermore, other infectious agents 102 that can be quantified can comprise fungi or mold including, but not limited to, *Candida* spp. (including but not limited to *Candida albicans, Candida glabrata, Candida tropicalis, Candida parapsilosis,* and *Candida krusei*), *Aspergillus* spp. (including but not limited to *Aspergillus fumigatous, Aspergillus flavus, Aspergillus clavatus*), *Cryptococcous* spp. (including but not limited to *Cryptococcus neoformans, Cryptococcus gattii, Cryptococcus laurentii,* and *Cryptococcus albidus*), *Fusarium* spp. (including but not limited to *Fusarium oxysporum, Fusarium solani, Fusarium verticillioides,* and *Fusarium proliferatum*), *Rhizopus oryzae, Penicillium marneffei, Coccidiodes immitis,* and *Blastomyces dermatitidis*.

The fluid delivery conduits 108 can include tubes, pumps, containers, or microfluidic channels for delivering buffers, reagents, fluid samples including the sample 104 or solubilized solutions thereof, other solutions, or a combination thereof to and between devices, apparatus, or containers in the system. For example, as shown in FIG. 1, the fluid delivery conduits 108 can refer to parts of a pump such as a syringe pump. In other embodiments, the fluid delivery conduits 108 can include or refer to at least part of a hydraulic pump, a pneumatic pump, a peristaltic pump, a vacuum pump or a positive pressure pump, a manual or mechanical pump, or a combination thereof. In additional embodiments, the fluid delivery conduits 108 can include or refer to at least part of an injection cartridge, a pipette, a capillary, or a combination thereof. The fluid delivery conduits 108 can also be part of a vacuum system configured to draw fluid to or through channels, tubes, or passageways under vacuum. Moreover, the fluid delivery conduits 108 can include or refer to at least part of a multichannel delivery system or pipette.

The method 100 can comprise diluting the sample 104 comprising the infectious agent 102 with a dilutive solution 110 to yield a diluted sample 112 in step 1B. In one embodiment, the dilutive solution 110 can comprise growth media or a growth inducer. In this and other embodiments, the dilutive solution 110 can be a solution containing bactotryptone, yeast extract, beef extract, cation-adjusted Mueller Hinton Broth (CAMHB), Mueller Hinton growth media (MHG), starch, acid hydrolysate of casein, calcium chloride, magnesium chloride, sodium chloride, blood or lysed blood including lysed horse blood (LHB), CAMHB-LHB, glucose, or a combination thereof. The growth inducer can comprise a carbon-based inducer, a nitrogen-based inducer, a mineral, a trace element, a biological growth factor, or any combination thereof. For example, the growth inducer can include but is not limited to glucose, ammonia, magnesium, blood, or a combination thereof. In one example embodiment, the dilutive solution 110 can comprise Tryptone, yeast extract, sodium chloride, and glucose. The dilutive solution 110 can be used to counteract the buffering effects of ions or substances present in the sample 104.

In one embodiment, diluting the sample 104 with the dilutive solution 110 in step 1B can involve diluting the sample 104 to a dilution ratio between about 1:1 to about 1:10. In another embodiment, diluting the sample 104 with the dilutive solution 110 can involve diluting the sample 104 to a dilution ratio between about 1:10 to about 1:100. In yet another embodiment, diluting the sample 104 with the dilutive solution 110 can involve diluting the sample 104 to a dilution ratio between about 1:100 to about 1:1000. In a further embodiment, diluting the sample 104 with the dilutive solution 110 can involve diluting the sample 104 to a dilution ratio between about 1:1000 to about 1:10000. Although FIG. 1 illustrates one reaction vessel 106 or one aliquot of the sample 104 being diluted, it is contemplated by this disclosure that multiple aliquots of the sample 104 can be diluted to different dilution ratios such that one or more diluted samples 112 can act as internal controls.

As will be discussed in the following sections in relation to FIGS. 2A, 2B, and 2C, in alternative embodiments, the method 100 can comprise diluting the sample 104 comprising the infectious agent 102 with deionized water, a saline solution, or a combination thereof serving as the dilutive solution 110. In these embodiments, the diluted sample(s) 112 can be introduced to one or more sensors through sample delivery conduits comprising growth media or a growth inducer such that the diluted sample 112 is mixed with the growth media or growth inducer. More details concerning these embodiments will be discussed in the following sections.

The method 100 can also comprise incubating the diluted sample 112 at an elevated temperature for a period of time in step 1C. The diluted sample 112 can be incubated in the same reaction vessel 106 or transferred to a different reaction vessel 106 or container. For example, the diluted sample 112 can be heated to a temperature of between about 30° C. and about 40° C. (e.g., 35° C.±2° C.) and allowed to incubate for an incubation period 114. The incubation period 114 can range from 15 minutes to over one hour. In other embodiments, the incubation period 114 can be less than 15 minutes or up to 48 hours.

The method 100 can further comprise introducing the diluted sample 112 to a sensor 116 or exposing the sensor 116 to the diluted sample 112 such that the diluted sample 112 is in fluid communication with a redox-active material 908 (see FIGS. 9A and 9B) of the sensor 116 in step 1D. In one or more embodiments, the sensor 116 can be an oxidation reduction potential (ORP) sensor configured to respond to a change in a solution characteristic (e.g., the ORP) of a measured solution. In the example embodiment shown in FIG. 1, exposing the sensor 116 to the diluted sample 112 can involve directly immersing at least part of a handheld or probe instance of the sensor 116 into the diluted sample 112. In this embodiment, the handheld or probe instance of the sensor 116 can be a handheld OPR sensor coupled to a standalone parameter analyzer 118 such as a voltmeter or multimeter. In another example embodiment shown in FIG. 2, introducing the diluted sample 112 to the sensor 116 can involve injecting, delivering, or otherwise introducing the diluted sample 112 to a well or container comprising the sensor 116 fabricated on a substrate. The sensor 116 will be discussed in more detail in the following sections.

The method 100 can further comprise monitoring the ORP of the diluted sample 112 with at least one parameter analyzer 118 coupled to the sensor 116 in step 1E. The ORP of the diluted sample 112 can be monitored in the absence of any added reporter molecules or exogenous reporter molecules in the diluted sample 112 in order to determine the concentration of the infectious agent 102 in the original sample 104.

The diluted sample 112 can have a solution characteristic. The solution characteristic of the diluted sample 112 can change as the amount of electro-active redox species changes due to the energy use, oxygen uptake or release, growth, or metabolism of the infectious agents 102 in the diluted sample 112. For example, the amount of electro-active redox species in the diluted sample 112 can change as a result of cellular activity (e.g., microbial aerobic or anaerobic respiration) undertaken by the infectious agents 102. As a more specific example, the amount of electron donors from Table 1 below (e.g., the amount of energy carriers such as nicotinamide adenine dinucleotide (NADH) and flavin adenine dinucleotide ($FADH_2$)) in the diluted sample 112 can change due to the growth of the infectious agents 102 in the diluted sample 112 within the reaction vessel 106. Also, as another more specific example, the amount of oxygen depleted in the diluted sample 112 due to aerobic respiration can change due to the growth of the infectious agents 102 in the diluted sample 112 within the reaction vessel 106.

TABLE 1

Below is a "redox tower" visualizing potential electron donors and acceptors which can be utilized by microorganisms or infectious agents during the course of metabolism. An electron donor will have a greater negative potential than the electron acceptor. In aerobic respiration for example, $O_2$ can serve as a terminal electron acceptor whereas in anaerobic respiration, the terminal electron acceptor can comprise $NO_3^-$, $Fe^{3+}$, $Mn^{4+}$, $SO_4^{2-}$, or $CO_2$.

| Electron Donor and Acceptor Pairs | Measured Standard Reduction Potential $E'_0$ (mV) | Standard Reduction Potential $E'_0$ (mV) range |
|---|---|---|
| Glucose ⇌ 2 Pyruvate + $2e^-$ | −720 | −700 −600 |
| Glucose ⇌ 6 $CO_2$ + $24e^-$ | −500 | −500 |
| $H_2$ ⇌ $2H^+$ + $2e^-$ | −420 | −400 |
| NADH ⇌ $NAD^+$ + $2e^-$ | −320 | −300 |
| 2 GSH ⇌ GSSG + $2e^-$ | −240 | −200 |
| $H_2S$ ⇌ $SO_4^{2-}$ + $8e^-$ | −220 | |
| $FADH_2$ ⇌ FAD + $2H^+$ + $2e^-$ | −220 | |
| Lactate ⇌ Pyruvate + $2e^-$ | −190 | −100 |
| Succinate ⇌ Fumarate + $2e^-$ | 33 | 0 |
| Cyt b (red) ⇌ Cyt b (ox) + $e^-$ | 80 | |
| Ubiquinol ⇌ Ubiquinone + $2e^-$ | 110 | 100 |
| Cyt c (red) ⇌ Cyt c (ox) + $e^-$ | 250 | 200 |
| Cyt a (red) ⇌ Cyt a (ox) + $e^-$ | 290 | |
| | | 300 |
| $NO_2^-$ + $H_2O$ ⇌ $NO_3^-$ + $2e^-$ | 420 | 400 |
| $NH_4^+$ + $H_2O$ ⇌ $NO_2^-$ + $6e^-$ | 440 | |
| $Mn^{2+}$ + $H_2O$ ⇌ $MnO_2$ + $2e^-$ | 460 | |
| | | 500 |
| | | 600 |
| ½ $N_2$ + $3H_2O$ ⇌ $NO_3^-$ + $5e^-$ | 740 | 700 |
| $Fe^{2+}$ ⇌ $Fe^{3+}$ + $1e^-$ | 770 | |
| $H_2O$ ⇌ ½ $O_2$ + $2H^+$ + $2e^-$ | 820 | 800 900 |

As illustrated in FIG. 1, the parameter analyzer 118 can be connected to or communicatively coupled to a device having a display 122 or a display component configured to display a read-out of the electrical characteristic of the sensor 116 representing the solution characteristic of the diluted sample 112. Such a device can be referred to as a reader 120. In certain embodiments, the reader 120 can be a mobile device, a handheld device, a tablet device, or a computing device such as a laptop or desktop computer and the display 122 can be a mobile device display, a handheld device display, a tablet display, or a laptop or desktop monitor. In these and other embodiments, the parameter analyzer 118 can wirelessly communicate a signal or result to the reader 120 or another computing device having the display 122. In other embodiments, the parameter analyzer 118 and the reader 120 can be integrated into one device.

The method 100 can further comprise monitoring the ORP of the diluted sample 112 over a period of time with the at least one parameter analyzer 118, the reader 120, or a combination thereof in step 1F. The parameter analyzer 118, the reader 120, or a combination thereof can also determine the concentration of the infectious agent 102 in the sample 104 within this period of time in step 1F. The period of time within which the parameter analyzer 118, the reader 120, or a combination thereof can determine the concentration of the infectious agent 102 can be referred to as a quantification window 124. In one embodiment, the quantification window 124 can be between 60 minutes and 120 minutes. In other embodiments, the quantification window 124 can be between 5 minutes and 60 minutes. In additional embodiments, the quantification window 124 can be greater than 120 minutes.

The parameter analyzer, the reader 120, or a combination thereof can determine the concentration of the infectious agent 102 in the sample 104 using measured ORP signals (e.g., measured output voltages) and a standard curve 126 generated by monitoring the ORPs of prepared cultures of the infectious agent in different concentrations. In some embodiments, the standard curve 126 can be generated before step 1A. In other embodiments, the standard curve 126 can be generated at any time prior to step 1F.

In one example embodiment, the standard curve 126 can be generated using different concentrations of bacteria (e.g., from about $1*10^4$ CFU/mL to about $1*10^8$ CFU/mL) grown at 35° C. in growth media. The ORPs of growth media comprising such bacterial concentrations can be monitored over time for a change in their ORPs using an ORP sensor. A threshold voltage can be set (e.g., between about −100 mV and 100 mV) and a standard curve can be generated by plotting the various bacterial concentrations against the time it took the monitored ORP of each such bacterial concentration to reach the threshold voltage (also known as the time-to-detection (TTD)). Generation of the standard curve is discussed in more detail in the following sections.

With the standard curve 126 generated, the method 100 can involve comparing the measured or monitored ORP of the diluted sample 112 over time against the values obtained from the standard curve 126. For example, as shown in FIG. 1, a growth curve 128 for the infectious agent 102 within the sample 104 under investigation can be generated using the change in ORP of the diluted sample 112 over time measured by the parameter analyzer 118, the reader 120, or a combination thereof. The same threshold voltage 130 can be applied to the growth curve 128 as the threshold voltage 130 used to generate the standard curve 126. The time-to-detection 132 or the time it took the monitored ORP of the diluted sample 112 to reach the threshold voltage 130 can be ascertained from the growth curve 128. The reader 120, the parameter analyzer 118, or another device can then determine the concentration of the infectious agent in the sample 104 under investigation by using the time-to-detection 132 and the values obtained from the standard curve 126. For example, the concentration can be calculated using the time-to-detection 132 and an equation derived from the standard curve 126.

In some embodiments, one or more of the aforementioned steps of the method 100 can be stored as machine-executable instructions or logical commands in a non-transitory machine-readable medium (e.g., a memory or storage unit) of the parameter analyzer 118, the reader 120, or another device communicatively or electrically coupled to the parameter analyzer 118 or the reader 120. Any of the parameter analyzer 118, the reader 120, or another device coupled to the parameter analyzer 118 or the reader 120 can comprise one or more processors or controllers configured to execute the aforementioned instructions or logical commands.

The steps depicted in FIG. 1 do not require the particular order shown to achieve the desired result. Moreover, certain steps or processes may be omitted or occur in parallel in order to achieve the desired result. In addition, any of the systems or devices disclosed herein can be used in lieu of devices or systems shown in the steps of FIG. 1.

Figure 2A:
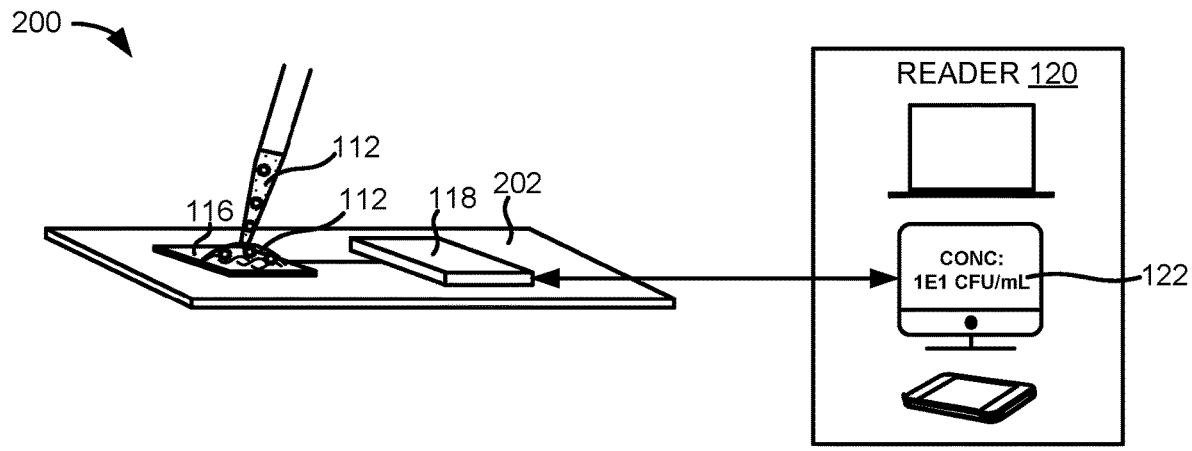
FIGS. 2A to 2C illustrate embodiments of systems for determining the concentration of one or more infectious agents in a biological sample.
Figure 2B:
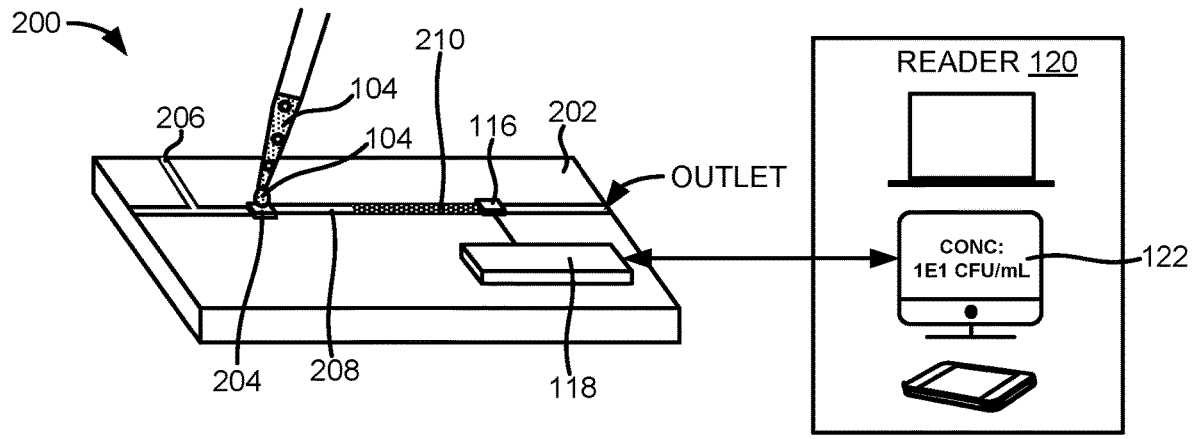
Figure 2C:
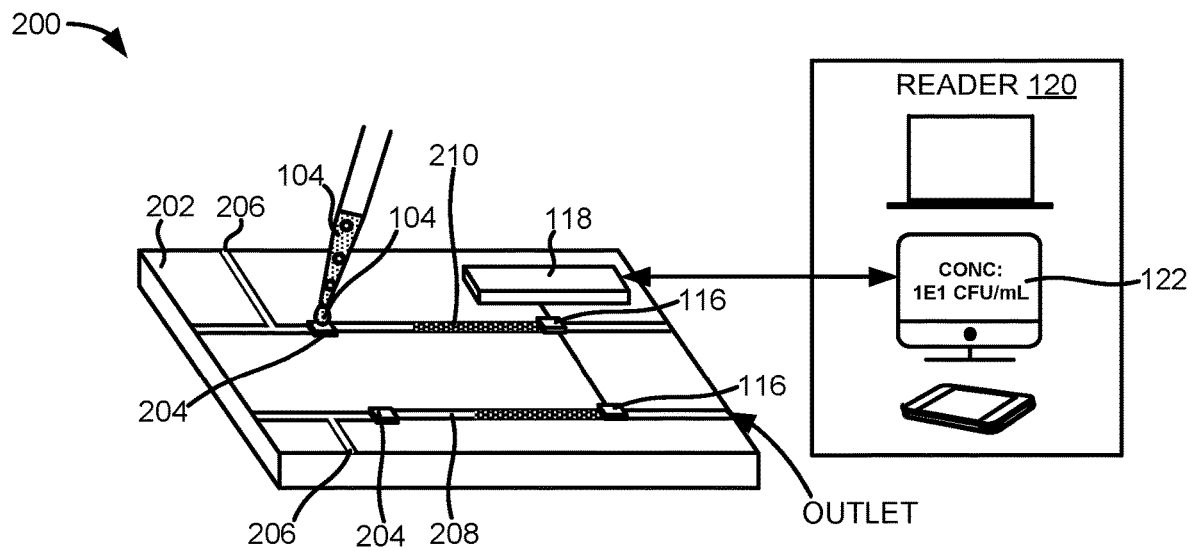

FIGS. 2A, 2B, and 2C illustrate embodiments of systems 200 for determining the concentration of one or more infectious agents 102 in a sample 104 (see FIG. 1). It is contemplated by this disclosure (and it should be understood by one or ordinary skill in the art) that any of the systems 200 described in connection with FIG. 2A, 2B, or 2C can be used to undertake one or more steps of the method 100 described in the preceding sections. FIG. 2A illustrates that the system 200 can comprise one or more sensors 116 fabricated or positioned on a surface of a substrate 202, one or more parameter analyzers 118 electrically or communicatively coupled to the one or more sensors 116, and one or more readers 120 electrically or communicatively coupled to the one or more parameter analyzers 118. In some embodiments, the reader 120 and the parameter analyzer 118 can be integrated into one device.

In some embodiments, the substrate 202 and the sensors 116 can be part of a cartridge, a test strip, an integrated circuit, a micro-electro-mechanical system (MEMS) device, a microfluidic chip, or a combination thereof. In these and other embodiments, the substrate 202 can be part of a lab-on-a-chip (LOC) device. In all such embodiments, the sensors 116 can comprise components of such circuits, chips, or devices including, but not limited to, one or more transistors, gates, or other electrical components. The sensors 116 can be micro- or nano-scale ORP sensors. Each of the sensors 116 can comprise an active electrode and a reference electrode (see FIGS. 9A and 9B). Each of the sensors 116 can also comprise a redox-active material 908 (see FIGS. 9A and 9B) or layer such as a gold layer, a platinum layer, a metal oxide layer, carbon layer, or a combination thereof. The sensors 116 will be discussed in more detail in the following sections.

In one embodiment, the sample 104 comprising the infectious agent 102 can be diluted using growth media or growth inducers representing the dilutive solution 110. The growth media or growth inducers can be the same growth media or growth inducers described with respect to step 1B of method 100. In this embodiment, the diluted sample 112 can be injected, pipetted, delivered, or otherwise introduced to the one or more sensors 116 such that the diluted sample 112 is in fluid communication with the redox-active material 908 (see FIGS. 9A and 9B) of the sensors 116.

The system 200 can also comprise an incubating component configured to incubate the diluted sample 112 in fluid communication with the sensor 116 by heating the diluted sample 112 to a temperature of between about 30° C. and about 40° C. (e.g., 35° C.±2° C.) for a period of time (e.g., the incubation period 114).

In another embodiment, the sample 104 comprising the infectious agent 102 can be diluted using deionized water, a saline solution, or a combination thereof representing the dilutive solution 110 to yield the diluted sample 112. In this embodiment, the one or more sensors 116 on the substrate 202 can be covered or coated by a lyophilized or dried form of the growth media or growth inducer. For example, the one or more sensors 116 can comprise a layer of lyophilized or dried growth media or growth inducer covering or coating the one or more sensors 116. In another embodiment, the lyophilized or dried growth inducer can cover or coat a surface in a vicinity of the one or more sensors 116. In yet another embodiment, the one or more sensors 116 can be disposed within a well or a container defined on the substrate 202 and the well or container can comprise an aqueous form of the growth media or growth inducer. In all such embodiments, the diluted sample 112 can mix with the growth media or growth inducer.

The incubating component can then incubate the diluted sample 112 mixed with the growth media or growth inducer by heating the mixture to a temperature of between about 30° C. and about 40° C. (e.g., 35° C.±2° C.) for a period of time (e.g., the incubation period 114).

FIG. 2B illustrates another embodiment of a system 200 for determining the concentration of one or more infectious agents 102 in a sample 104. The system 200 can comprise a sample receiving surface 204 defined on a substrate 202, one or more metering conduits 206 in fluid communication with the sample receiving surface 204, a sensor 116 fabricated or otherwise disposed on the substrate 202, one or more sample delivery conduits 208 fluidly connecting or extending in between the sample receiving surface 204 and the sensor 116, a parameter analyzer 118 electrically or communicatively coupled to the sensor 116, and a reader 120 electrically or communicatively coupled to the parameter analyzer 118. In some embodiments, the reader 120 and the parameter analyzer 118 can be integrated into one device.

In one or more embodiments, the sample receiving surface 204 can be a flat surface for receiving the sample 104. In other embodiments, the sample receiving surface 204 can be a concave or tapered surface of a well, divot, dish, or container. For example, the sample 104 can be injected, pipetted, pumped, spotted, or otherwise introduced to the sample receiving surface 204.

The one or more metering conduits 206 can be channels, passageways, capillaries, tubes, parts therein, or combinations thereof for delivering the dilutive solution 110 to the sample 104 on the sample receiving surface 204. For example, the one or more metering conduits 206 can refer to channels, passageways, capillaries, or tubes defined on the substrate 202. Also, for example, the one or more metering conduits 206 can refer to channels, passageways, capillaries, or tubes serving as part of hydraulic pump, a pneumatic pump, peristaltic pump, a vacuum or positive pressure pump, a manual or mechanical pump, a syringe pump, or a combination thereof. For example, the one or more metering conduits 206 can be microfluidic channels or tubes or channels serving as part of a vacuum system.

In some embodiments, the one or more metering conduits 206 can be configured to dilute the sample 104 with the dilutive solution 110 to a dilution ratio between about 1:1 to about 1:10. In other embodiments, the one or more metering conduits 206 can be configured to dilute the sample 104 with the dilutive solution 110 to a dilution ratio between about 1:10 to about 1:100. In additional embodiments, the one or more metering conduits 206 can be configured to dilute the sample 104 with the dilutive solution 110 to a dilution ratio between about 1:100 to about 1:1000. In yet additional embodiments, the one or more metering conduits 206 can be configured to dilute the sample 104 with the dilutive solution 110 to a dilution ratio between about 1:1000 to about 1:10000.

The one or more sample delivery conduits 208 can be channels, passageways, capillaries, tubes, parts therein, or combinations thereof for delivering the diluted sample 112 to the sensor 116. For example, the one or more sample delivery conduits 208 can fluidly connect the sample receiving surface 204 with the sensor 116 such that the diluted sample 112 or fluid on the sample receiving surface 204 is in fluid communication with at least part of the sensor 116.

As shown in the example embodiment of FIG. 2B, the one or more sample delivery conduits 208 can comprise growth media 210 or growth inducer. The growth media 210 or growth inducer can be the same growth media or growth inducer discussed in connection with FIG. 2A and FIG. 1.

In one or more embodiments, the sample delivery conduits 208 can be covered or coated by a lyophilized or dried form of the growth media 210 or the growth inducer. In other embodiments, the sample delivery conduits 208 can contain growth media 210 or grow inducer in an aqueous form. In these and other embodiments, the dilutive solution 110 delivered by the one or more metering conduits 206 can be a saline solution, deionized water, or a combination thereof. The dilutive solution 110 can dilute the sample 104 and deliver the sample 104 through the sample delivery conduits 208 to the sensor 116 such that the diluted sample 112 mixes with the growth media 210 en route to the sensor 116. In other embodiments not shown in the figures, at least one layer of the sensor 116 or a surface in a vicinity of the sensor 116 can be coated or covered by the growth media 210 in lyophilized or dried form and the diluted sample 112 can mix with the growth media 210 when the diluted sample 112 is in fluid communication with the part of the sensor 116 or part of the area covered by the growth media 210.

In all such embodiments, the diluted sample 112 can mix with the growth media 210 or growth inducer.

The incubating component can then incubate the diluted sample 112 mixed with the growth media 210 or growth inducer by heating the mixture to a temperature of between about 30° C. and about 40° C. (e.g., 35° C.±2° C.) for a period of time (e.g., the incubation period 114).

In some embodiments, the substrate 202 and sensors 116 can be part of a cartridge, a test strip, an integrated circuit, a micro-electro-mechanical system (MEMS) device, a microfluidic chip, or a combination thereof. In these and other embodiments, the substrate 202 can be part of a lab-on-a-chip (LOC) device. In all such embodiments, the sensor 116 can comprise components of such circuits, chips, or devices including, but not limited to, one or more transistors, gates, or other electrical components. The sensor 116 can be a micro- or nano-scale ORP sensor. The sensor 116 can comprise an active electrode and a reference electrode. The sensor 116 can also comprise a redox-active material 908 (see FIGS. 9A and 9B) or layer such as a gold layer, a platinum layer, a metal oxide layer, carbon layer, or a combination thereof. The sensor 116 will be discussed in more detail in the following sections.

FIG. 2C illustrates a multiplex version of the system 200 shown in FIG. 2B. For example, the system 200 of FIG. 2C can have multiple sensors 116, multiple metering conduits 206, and multiple sample delivery conduits 208. In one embodiment, different samples comprising different types of infectious agents can be delivered, injected, or otherwise introduced to the various sample receiving surfaces 204 on one substrate 202.

The substrate 202 can be comprised of a polymeric material, a metal, a ceramic, a semiconductor layer, an oxide layer, an insulator, or a combination thereof. The substrate 202 can be part of a test strip, cartridge, chip or lab-on-a-chip, microfluidic device, multi-well container, or a combination thereof. The sensors 116 can be fabricated or located on a surface of the substrate 202. In some embodiments, the one or more parameter analyzers 118 can also be fabricated or located on the substrate 202. In other embodiments, the one or more parameter analyzers 118 can be standalone devices such as a voltmeter or a multimeter electrically coupled to the sensors 116.

In this embodiment, the system 200 shown in FIG. 2C can be used to determine the concentrations of infectious agents 102 in multiple samples concurrently. In other embodiments, aliquots of the same sample 104 can be introduced to the various sample receiving surfaces 204 on one substrate 202 and different amounts of the dilutive solution 110 can be delivered to the various sample receiving surfaces 204 through the metering conduits 206. In this embodiment, the multiplex system 200 of FIG. 2C can be used to dilute aliquots of the same sample 104 to different dilution ratios so as to use certain dilutions as internal controls and to determine the minimum amount of dilution needed to quantify a certain sample.

In the example embodiments shown in FIGS. 2A, 2B, and 2C, the one or more parameter analyzers 118 can be disposed or fabricated on the substrate 202 or the parameter analyzers 118 can also be standalone devices coupled to the one or more sensors 116. The parameter analyzers 118 can be electrically or communicatively coupled to one or more readers 120 having a display 122 or display component. The display 122 or display component can be configured to display a read-out of the electrical characteristic of the one or more sensors 116 representing the solution characteristic of the diluted sample 112. In certain embodiments, the reader 120 can be a mobile device, a handheld device, a tablet device, or a computing device such as a laptop or desktop computer and the display 122 can be a mobile device display, a handheld device display, a tablet display, or a laptop or desktop monitor. In some embodiments, the parameter analyzer 118 can wirelessly communicate a signal or result to the reader 120 or another computing device having the display 122.

Similar to step 1F of method 100, the systems 200 of FIGS. 2A, 2B, and 2C can monitor the ORP of the diluted sample 112 and determine the concentration of the infectious agent 102 in the sample 104 within a period of time (e.g., the quantification window 124 of method 100). This period of time can be between 60 minutes and 120 minutes. In other embodiments, this period of time can be between 5 minutes and 60 minutes. In additional embodiments, this period of time can be greater than 120 minutes.

The parameter analyzer 118, the reader 120, or another device in communication with the parameter analyzer 118 or the reader 120 can determine the concentration of the infectious agent 102 in the sample 104 using measured ORP signals (e.g., measured output voltages) and a standard curve (such as the standard curve 126 described in connection with method 100 of FIG. 1). In one example embodiment, a standard curve can be generated using different concentrations of bacteria (e.g., from about $1*10^4$ CFU/mL to about $1*10^8$ CFU/mL) grown at 35° C. in growth media. The ORPs of growth media comprising such bacterial concentrations can be monitored over time for a change in their ORPs using one or more ORP sensors. A threshold voltage can be set (e.g., between about −100 mV and 100 mV) and a standard curve can be generated by plotting the various bacterial concentrations against the time it took the monitored ORP of each such bacterial concentration to reach the threshold voltage (also known as the time-to-detection (TTD)). Generation of the standard curve is discussed in more detail in the following sections.

The reader 120, the parameter analyzer 118, or another device in communication with either the reader 120 or the parameter analyzer 118 can compare the measured or monitored ORP of the diluted sample 112 over time against the values obtained from the standard curve. The reader 120, the parameter analyzer or another device in communication with either the reader 120 or the parameter analyzer 118 can then determine the concentration of the infectious agent 102 in the sample 104 under investigation by using the time-to-detection and the values obtained from the standard curve. For example, the concentration can be calculated using the time-to-detection and an equation derived from the standard curve.

In some embodiments, one or more of the aforementioned steps can be stored as machine-executable instructions or logical commands in a non-transitory machine-readable medium (e.g., a memory or storage unit) of the parameter analyzer 118, the reader 120, or another device communicatively or electrically coupled to the parameter analyzer 118 or the reader 120. Any of the parameter analyzer 118, the reader 120, or another device coupled to the parameter analyzer 118 or the reader 120 can comprise one or more processors or controllers configured to execute the aforementioned instructions or logical commands. In addition, any of the devices or systems shown in the example embodiments of FIGS. 2A, 2B, and 2C can be used to perform steps or operations of methods disclosed herein including, but not limited to, methods 100 and 500.

Figure 3A:
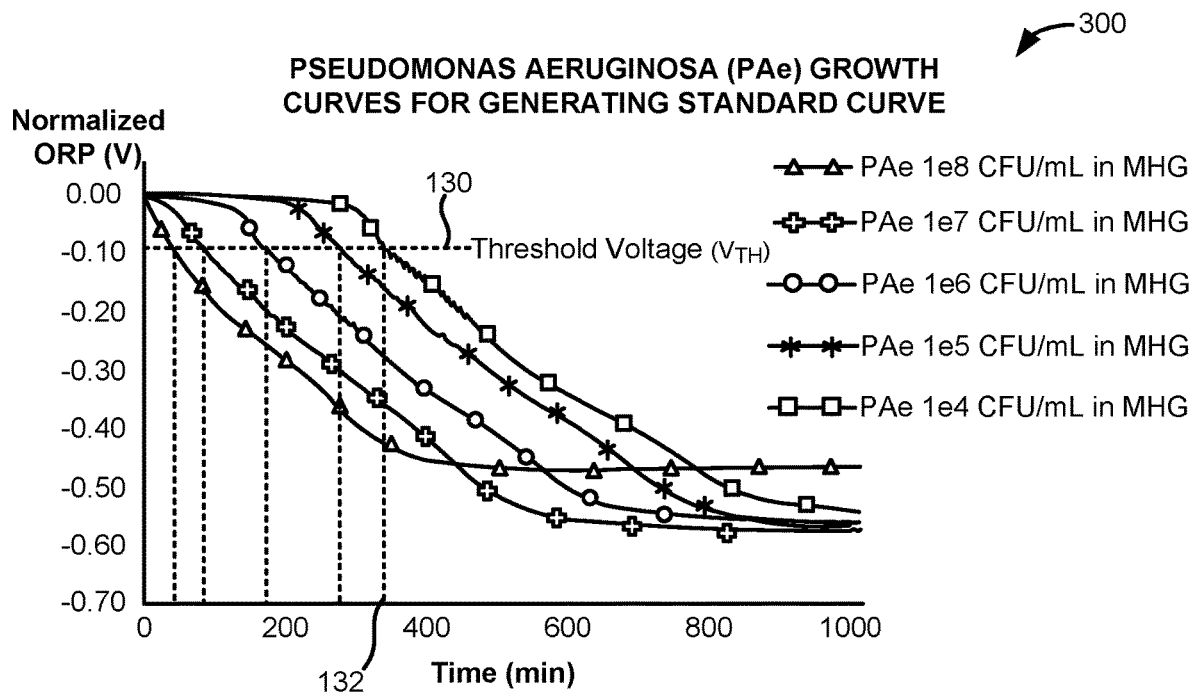
FIG. 3A illustrates example growth curves used to generate a standard curve for determining the concentration of one or more infectious agents in a biological sample.

FIG. 3A illustrates bacterial growth curves obtained by monitoring the change in ORP of growth media comprising different concentrations (e.g., from about $1*10^4$ CFU/mL to about $1*10^8$ CFU/mL) of a type of bacteria. For example, FIG. 3A illustrates growth curves of different concentrations of *Pseudomonas aeruginosa* (PAe) bacteria grown at 35° C. in Mueller Hinton growth media (MHG). The ORPs of growth media exposed to the various PAe concentrations were monitored using ORP sensors (for example, any of the sensors 116 of FIGS. 1, 2A, 2B, and 2C). A threshold voltage 130 was set at −100 mV and the time it took the monitored ORPs to reach the threshold voltage 130 (i.e., the TTDs 132) were used to generate the standard curve 126.

Figure 3B:
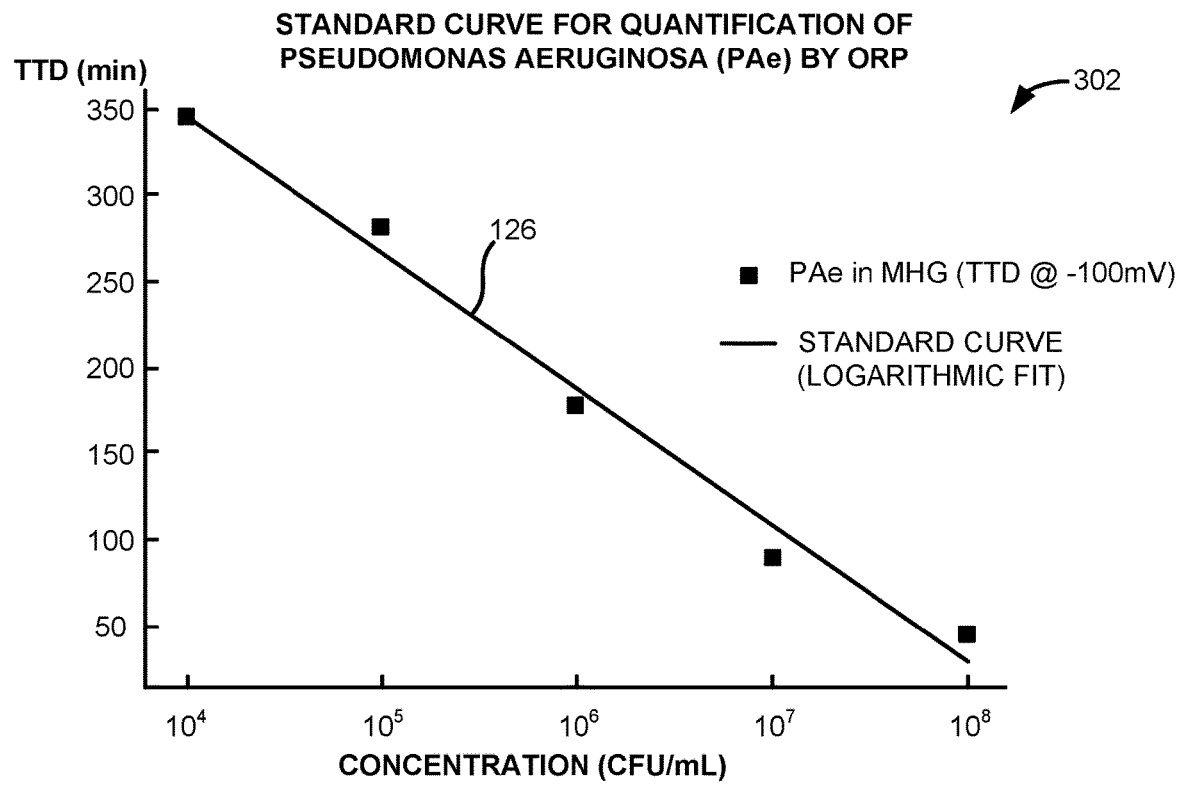
FIG. 3B illustrates a fitted standard curve for determining the concentration of one or more infectious agents in a biological sample.

FIG. 3B illustrates a standard curve 126 generated using certain experimental data from the experiments described above. As shown in FIG. 3B, a threshold ORP level was set at −100 mV. The various TTDs 132 were plotted as a function of the logarithm of the known concentration of the infectious agent 102 present in the various samples. A standard curve 126 can then be generated using curve fitting techniques such as logarithmic regression and least-squares. In other embodiments, polynomial and logarithmic curve fitting techniques can also be used.

As shown in FIG. 3B, a logarithmic standard curve 126 can be generated using values obtained from monitoring the ORP of growth media exposed to various concentrations of an infectious agent 102. Deriving an equation for this logarithmic standard curve 126 can then allow us to interpolate unknown concentrations of infectious agents 102 in a sample using only the time it took such a solution to reach the ORP threshold voltage 130.

Figure 4:
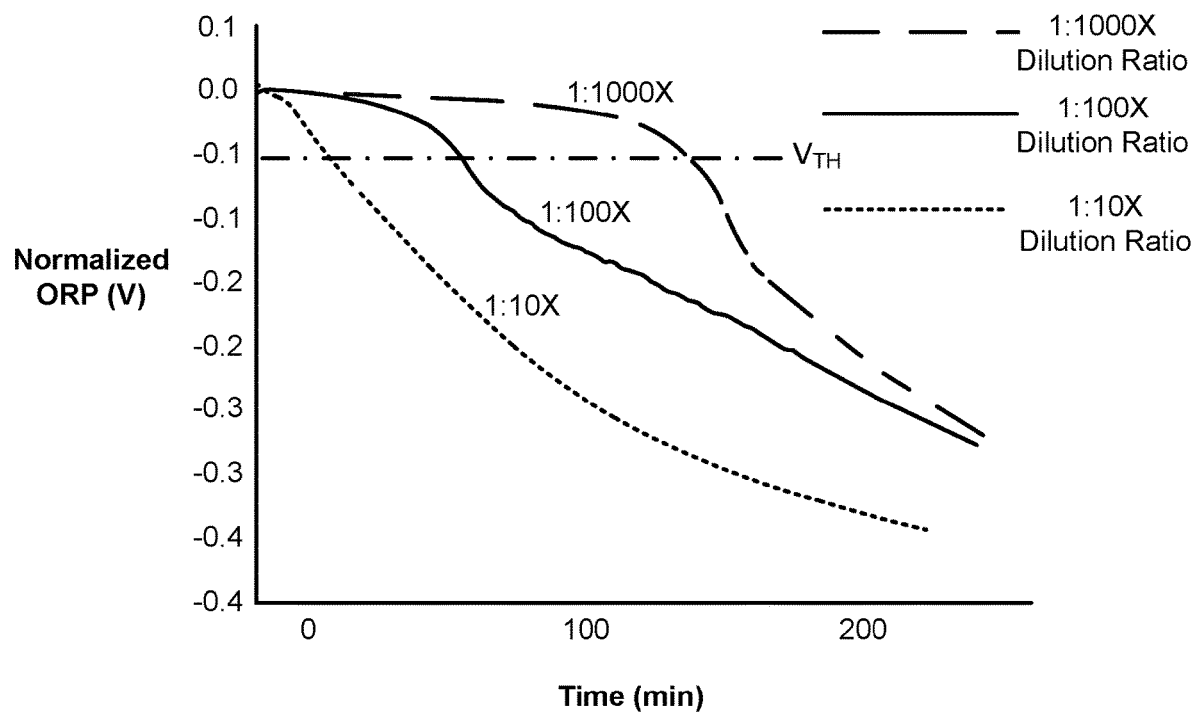
FIG. 4 illustrates example bacterial growth curves used to determine the concentration of the bacteria in a sample.

FIG. 4 illustrates bacterial growth curves used in the quantification of PAe from positive blood cultures. The positive blood cultures were prepared by adding 10 CFU/mL of PAe to 25 mL of human blood. The resulting blood comprising PAe was then added to 30 mL of blood culture media (e.g., 30 mL of BD BACTEC™ Plus Aerobic Medium). The combined mixture of human blood containing PAe and blood culture media was then grown to positivity. Three aliquots of the positive blood culture were then diluted with growth media to dilution ratios of 1:10, 1:100, and 1:1000, respectively. Such diluted samples were then introduced to an ORP sensor comprising a redox-active material. FIG. 4 illustrates changes in the ORP signals of the three diluted samples over time (commonly referred to as bacterial growth curves). As shown in FIG. 4, a threshold voltage of −100 mV was set and the time-to-detection of each curve was measured and compared to the PAe standard curve of FIG. 3B. The concentration of the PAe (in CFU/mL) can then be determined using the standard curve and by taking into account the amount of dilution. Diluting the positive blood culture with growth media to different dilution ratios can be helpful in determining the minimum amount of dilution needed to quantify a certain sample and ensuring that all such concentration determinations ultimately align.

Figure 5:
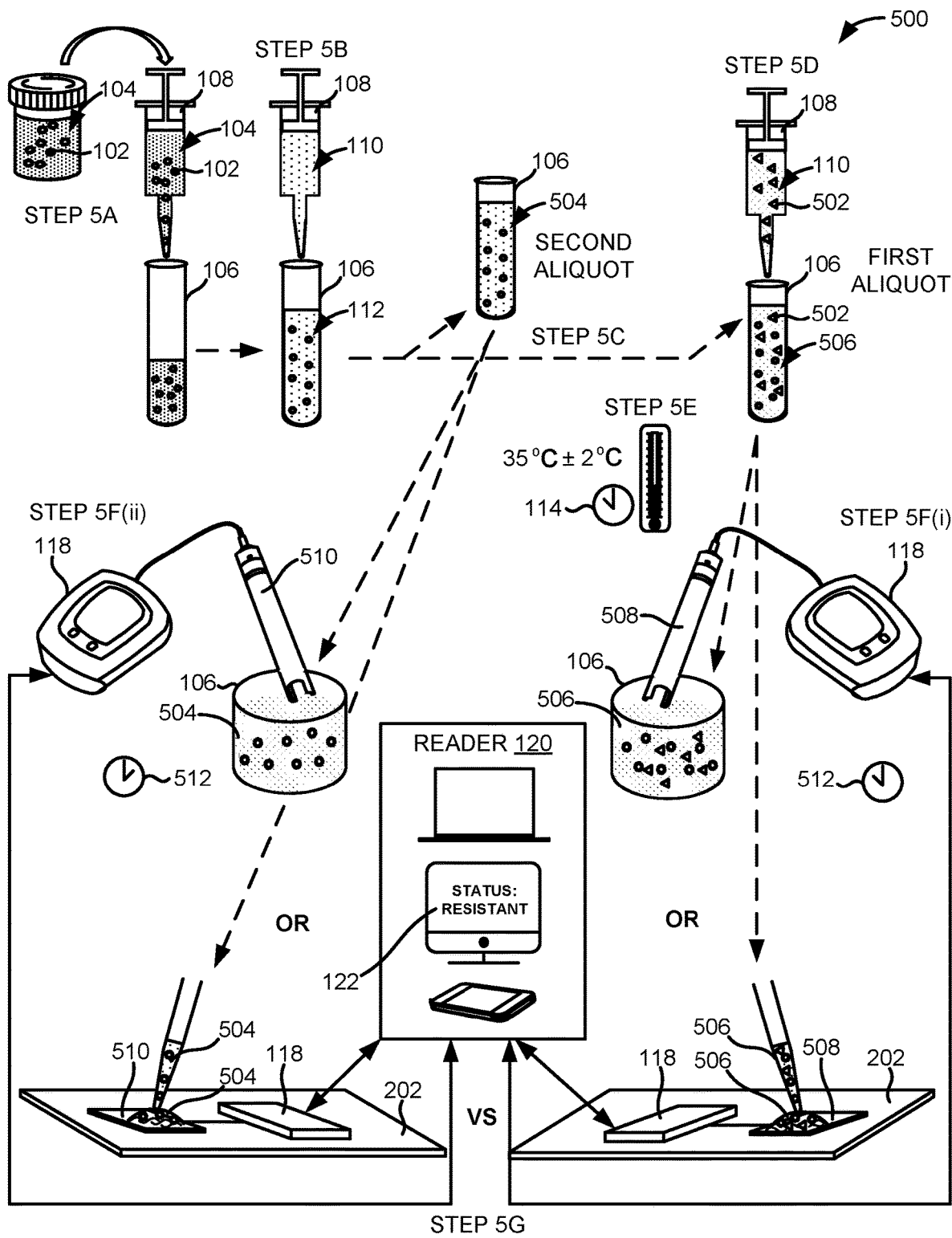
FIG. 5 illustrates one embodiment of a method for determining the susceptibility of one or more infectious agents to one or more anti-infectives.

FIG. 5 illustrates an embodiment of a method 500 for determining the susceptibility of one or more infectious agents 102 in a sample 104 to one or more anti-infectives 502. The method 500 can comprise introducing one or more aliquots of the sample 104 into one or more reaction vessels 106 in step 5A. The reaction vessels 106 can refer to one or more test tubes, reaction tubes, wells of a high throughput assay plate or well plate such as a 96-well plate, a 192-well plate, or a 384-well plate, culture plates or dishes, or other suitable containers for housing biological samples. One or more fluid delivery conduits 108 can introduce, deliver, or otherwise introduce the aliquots of the sample 104 to the one or more reaction vessels 106.

In other embodiments not shown in FIG. 5, a stimulus solution can be added to the sample 104 before introducing the sample 104 to the reaction vessel 106. The stimulus solution can be a nutrient or growth solution. In these and other embodiments, the sample 104 can also be filtered before step 5A. This filtering step can involve filtering the sample 104 using an instance of a filter, a microfluidic filter, or a combination thereof to filter out debris, inorganic material, and larger cellular components including blood cells or epithelial cells from the sample 104.

The sample 104 can comprise at least one of a biological sample, a bodily fluid, a wound swab or sample, a rectal swab or sample, and a bacterial culture derived from the biological sample, the bodily fluid, the wound swab or sample, or the rectal swab or sample. The bodily fluid can comprise urine, blood, serum, plasma, saliva, sputum, semen, breast milk, joint fluid, spinal fluid, wound material, mucus, fluid accompanying stool, re-suspended rectal or wound swabs, vaginal secretions, cerebrospinal fluid, synovial fluid, pleural fluid, peritoneal fluid, pericardial fluid, amniotic fluid, cultures of bodily which has been tested positive for bacteria or bacterial growth such as blood culture which has been tested positive for bacteria or bacterial growth (i.e., positive blood culture), or a combination thereof.

The infectious agents 102 that can be assayed for anti-infective susceptibility using the methods or systems disclosed herein can be any metabolizing single- or multi-cellular organism including bacteria and fungi. In certain embodiments, the infectious agent 102 can be bacteria selected from the genera *Acinetobacter, Acetobacter, Actino-*

*myces, Aerococcus, Aeromonas, Agrobacterium, Anaplasma, Azorhizobium, Azotobacter, Bacillus, Bacteroides, Bartonella, Bordetella, Borrelia, Brucella, Burkholderia, Calymmatobacterium, Campylobacter, Chlamydia, Chlamydophila, Citrobacter, Clostridium, Corynebacterium, Coxiella, Ehrlichia, Enterobacter, Enterococcus, Escherichia, Francisella, Fusobacterium, Gardnerella, Haemophilus, Helicobacter, Klebsiella, Lactobacillus, Legionella, Listeria, Methanobacterium, Microbacterium, Micrococcus, Morganella, Moraxella, Mycobacterium, Mycoplasma, Neisseria, Pandoraea, Pasteurella, Peptostreptococcus, Porphyromonas, Prevotella, Proteus, Providencia, Pseudomonas, Ralstonia, Raoultella, Rhizobium, Rickettsia, Rochalimaea, Rothia, Salmonella, Serratia, Shewanella, Shigella, Spirillum, Staphylococcus, Strenotrophomonas, Streptococcus, Streptomyces, Treponema, Vibrio, Wolbachia, Yersinia*, or a combination thereof. In other embodiments, the infectious agent 102 can be one or more fungi selected from the genera *Candida* or *Cryptococcus* or mold.

Other specific bacteria that can be assayed for anti-infective susceptibility using the methods and systems disclosed herein can comprise *Staphylococcus aureus, Staphylococcus lugdunensis*, coagulase-negative *Staphylococcus* species (including but not limited to *Staphylococcus epidermidis, Staphylococcus haemolyticus, Staphylococcus hominis, Staphylococcus capitis*, not differentiated), *Enterococcus faecalis, Enterococcus faecium* (including but not limited to *Enterococcus faecium* and other *Enterococcus* spp., not differentiated, excluding *Enterococcus faecalis*), *Streptococcus pneumoniae, Streptococcus pyogenes, Streptococcus agalactiae, Streptococcus* spp., (including but not limited to *Streptococcus mitis, Streptococcus pyogenes, Streptococcus gallolyticus, Streptococcus agalactiae, Streptococcus pneumoniae*, not differentiated), *Pseudomonas aeruginosa, Acinetobacter baumannii, Klebsiella* spp. (including but not limited to *Klebsiella pneumoniae, Klebsiella oxytoca*, not differentiated), *Escherichia coli, Enterobacter* spp. (including but not limited to *Enterobacter cloacae, Enterobacter aerogenes*, not differentiated), *Proteus* spp. (including but not limited to *Proteus mirabilis, Proteus vulgaris*, not differentiated), *Citrobacter* spp. (including but not limited to *Citrobacter freundii, Citrobacter koseri*, not differentiated), *Serratia marcescens, Candida albicans*, and *Candida glabrata*.

Other more specific bacteria that can be assayed for anti-infective susceptibility can comprise *Acinetobacter baumannii, Actinobacillus* spp., *Actinomycetes, Actinomyces* spp. (including but not limited to *Actinomyces israelii* and *Actinomyces naeslundii*), *Aeromonas* spp. (including but not limited to *Aeromonas hydrophila, Aeromonas veronii* biovar *sobria* (*Aeromonas sobria*), and *Aeromonas caviae*), *Anaplasma phagocytophilum, Alcaligenes xylosoxidans, Actinobacillus actinomycetemcomitans, Bacillus* spp. (including but not limited to *Bacillus anthracis, Bacillus cereus, Bacillus subtilis, Bacillus thuringiensis*, and *Bacillus stearothermophilus*), *Bacteroides* spp. (including but not limited to *Bacteroides fragilis*), *Bartonella* spp. (including but not limited to *Bartonella bacilliformis* and *Bartonella henselae*), *Bifidobacterium* spp., *Bordetella* spp. (including but not limited to *Bordetella pertussis, Bordetella parapertussis*, and *Bordetella bronchiseptica*), *Borrelia* spp. (including but not limited to *Borrelia recurrentis*, and *Borrelia burgdorferi*), *Brucella* sp. (including but not limited to *Brucella abortus, Brucella canis, Brucella melintensis* and *Brucella suis*), *Burkholderia* spp. (including but not limited to *Burkholderia pseudomallei* and *Burkholderia cepacia*), *Campylobacter* spp. (including but not limited to *Campylobacter jejuni, Campylobacter coli, Campylobacter lari* and *Campylobacter fetus*), *Capnocytophaga* spp., *Cardiobacterium hominis, Chlamydia trachomatis, Chlamydophila pneumoniae, Chlamydophila psittaci, Citrobacter* spp. *Coxiella burnetii, Corynebacterium* spp. (including but not limited to, *Corynebacterium diphtheriae, Corynebacterium jeikeum* and *Corynebacterium*), *Clostridium* spp. (including but not limited to *Clostridium perfringens, Clostridium difficile, Clostridium botulinum* and *Clostridium tetani*), *Eikenella corrodens, Enterobacter* spp. (including but not limited to *Enterobacter aerogenes, Enterobacter agglomerans, Enterobacter cloacae* and *Escherichia coli*, including opportunistic *Escherichia coli*, including but not limited to enterotoxigenic *E. coli*, enteroinvasive *E. coli*, enteropathogenic *E. coli*, enterohemorrhagic *E. coli*, enteroaggregative *E. coli* and uropathogenic *E. coli*) *Enterococcus* spp. (including but not limited to *Enterococcus faecalis* and *Enterococcus faecium*) *Ehrlichia* spp. (including but not limited to *Ehrlichia chafeensia* and *Ehrlichia canis*), *Erysipelothrix rhusiopathiae, Eubacterium* spp., *Francisella tularensis, Fusobacterium nucleatum, Gardnerella vaginalis, Gemella morbillorum, Haemophilus* spp. (including but not limited to *Haemophilus influenzae, Haemophilus ducreyi, Haemophilus aegyptius, Haemophilus parainfluenzae, Haemophilus haemolyticus* and *Haemophilus parahaemolyticus*), *Helicobacter* spp. (including but not limited to *Helicobacter pylori, Helicobacter cinaedi* and *Helicobacter fennelliae*), *Kingella kingii, Klebsiella* spp. (including but not limited to *Klebsiella pneumoniae, Klebsiella granulomatis* and *Klebsiella oxytoca*), *Lactobacillus* spp., *Listeria monocytogenes, Leptospira interrogans, Legionella pneumophila, Leptospira interrogans, Peptostreptococcus* spp., *Moraxella catarrhalis, Morganella* spp., *Mobiluncus* spp., *Micrococcus* spp., *Mycobacterium* spp. (including but not limited to *Mycobacterium leprae, Mycobacterium tuberculosis, Mycobacterium intracellulare, Mycobacterium avium, Mycobacterium bovis*, and *Mycobacterium marinum*), *Mycoplasm* spp. (including but not limited to *Mycoplasma pneumoniae, Mycoplasma hominis*, and *Mycoplasma genitalium*), *Nocardia* spp. (including but not limited to *Nocardia asteroides, Nocardia cyriacigeorgica* and *Nocardia brasiliensis*), *Neisseria* spp. (including but not limited to *Neisseria gonorrhoeae* and *Neisseria meningitidis*), *Pasteurella multocida, Plesiomonas shigelloides*. *Prevotella* spp., *Porphyromonas* spp., *Prevotella melaninogenica, Proteus* spp. (including but not limited to *Proteus vulgaris* and *Proteus mirabilis*), *Providencia* spp. (including but not limited to *Providencia alcalifaciens, Providencia rettgeri* and *Providencia stuartii*), *Pseudomonas aeruginosa, Propionibacterium acnes, Rhodococcus equi, Rickettsia* spp. (including but not limited to *Rickettsia rickettsii, Rickettsia akari* and *Rickettsia prowazekii, Orientia tsutsugamushi* (formerly: *Rickettsia tsutsugamushi*) and *Rickettsia typhi*), *Rhodococcus* spp., *Serratia marcescens, Stenotrophomonas maltophilia, Salmonella* spp. (including but not limited to *Salmonella enterica, Salmonella typhi, Salmonella paratyphi, Salmonella enteritidis, Salmonella cholerasuis* and *Salmonella typhimurium*), *Serratia* spp. (including but not limited to *Serratia marcesans* and *Serratia liquifaciens*), *Shigella* spp. (including but not limited to *Shigella dysenteriae, Shigella flexneri, Shigella boydii* and *Shigella sonnei*), *Staphylococcus* spp. (including but not limited to *Staphylococcus aureus, Staphylococcus epidermidis, Staphylococcus hemolyticus, Staphylococcus saprophyticus*), *Streptococcus* spp. (including but not limited to *Streptococcus pneumoniae* (for example chloramphenicol-resistant serotype 4 *Streptococ-*

*cus pneumoniae*, spectinomycin-resistant serotype 6B *Streptococcus pneumoniae*, streptomycin-resistant serotype 9V *Streptococcus pneumoniae*, erythromycin-resistant serotype 14 *Streptococcus pneumoniae*, optochin-resistant serotype 14 *Streptococcus pneumoniae*, rifampicin-resistant serotype 18C *Streptococcus pneumoniae*, tetracycline-resistant serotype 19F *Streptococcus pneumoniae*, penicillin-resistant serotype 19F *Streptococcus pneumoniae*, and trimethoprim-resistant serotype 23F *Streptococcus pneumoniae*, chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, optochin-resistant serotype 14 *Streptococcus pneumoniae*, rifampicin-resistant serotype 18C *Streptococcus pneumoniae*, penicillin-resistant serotype 19F *Streptococcus pneumoniae*, or trimethoprim-resistant serotype 23F *Streptococcus pneumoniae*), *Streptococcus agalactiae, Streptococcus mutans, Streptococcus pyogenes*, Group A streptococci, *Streptococcus pyogenes*, Group B streptococci, *Streptococcus agalactiae*, Group C streptococci, *Streptococcus anginosus, Streptococcus equismilis*, Group D streptococci, *Streptococcus bovis*, Group F streptococci, and *Streptococcus anginosus* Group G streptococci), *Spirillum minus, Streptobacillus moniliformi, Treponema* spp. (including but not limited to *Treponema carateum, Treponema petenue, Treponema pallidum* and *Treponema endemicum, Tropheryma whippelii, Ureaplasma urealyticum, Veillonella* sp., *Vibrio* spp. (including but not limited to *Vibrio cholerae, Vibrio parahemolyticus, Vibrio vulnificus, Vibrio parahaemolyticus, Vibrio vulnificus, Vibrio alginolyticus, Vibrio mimicus, Vibrio hollisae, Vibrio fluvialis, Vibrio metchnikovii, Vibrio damsela* and *Vibrio furnisii*), *Yersinia* spp. (including but not limited to *Yersinia enterocolitica, Yersinia pestis*, and *Yersinia pseudotuberculosis*) and *Xanthomonas maltophilia* among others.

Furthermore, other infectious agents 102 that can be assayed for anti-infective susceptibility can comprise fungi or mold including, but not limited to, *Candida* spp. (including but not limited to *Candida albicans, Candida glabrata, Candida tropicalis, Candida parapsilosis*, and *Candida krusei*), *Aspergillus* spp. (including but not limited to *Aspergillus fumigatous, Aspergillus flavus, Aspergillus clavatus*), *Cryptococcous* spp. (including but not limited to *Cryptococcus neoformans, Cryptococcus gattii, Cryptococcus laurentii*, and *Cryptococcus albidus*), *Fusarium* spp. (including but not limited to *Fusarium oxysporum, Fusarium solani, Fusarium verticillioides*, and *Fusarium proliferatum*), *Rhizopus oryzae, Penicillium marneffei, Coccidiodes immitis*, and *Blastomyces dermatitidis*.

The fluid delivery conduits 108 can include tubes, pumps, containers, or microfluidic channels for delivering buffers, reagents, fluid samples including the sample 104 or solubilized solutions thereof, other solutions, or a combination thereof to and between devices, apparatus, or containers in the system. For example, as shown in FIG. 5, the fluid delivery conduits 108 can refer to parts of a pump such as a syringe pump. In other embodiments, the fluid delivery conduits 108 can include or refer to at least part of a hydraulic pump, a pneumatic pump, a peristaltic pump, a vacuum pump or a positive pressure pump, a manual or mechanical pump, or a combination thereof. In additional embodiments, the fluid delivery conduits 108 can include or refer to at least part of an injection cartridge, a pipette, a capillary, or a combination thereof. The fluid delivery conduits 108 can also be part of a vacuum system configured to draw fluid to or through channels, tubes, or passageways under vacuum. Moreover, the fluid delivery conduits 108 can include or refer to at least part of a multichannel delivery system or pipette.

The method 500 can comprise diluting the sample 104 comprising the one or more infectious agents 102 with a dilutive solution 110 to yield a diluted sample 112 in step 5B. In one embodiment, the dilutive solution 110 can comprise growth media or a growth inducer. In this and other embodiments, the dilutive solution 110 can be a solution containing bacto-tryptone, yeast extract, beef extract, cation-adjusted Mueller Hinton Broth (CAMHB), Mueller Hinton growth media (MHG), starch, acid hydrolysate of casein, calcium chloride, magnesium chloride, sodium chloride, blood or lysed blood including lysed horse blood (LHB), CAMHB-LHB, glucose, or a combination thereof. The growth inducer can comprise a carbon-based inducer, a nitrogen-based inducer, a mineral, a trace element, a biological growth factor, or any combination thereof. For example, the growth inducer can include but is not limited to glucose, ammonia, magnesium, blood, or a combination thereof. In one example embodiment, the dilutive solution 110 can comprise Tryptone, yeast extract, sodium chloride, and glucose. The dilutive solution 110 can be used to counteract the buffering effects of ions or substances present in the sample 104.

In one embodiment, diluting the sample 104 with the dilutive solution 110 in step 5B can involve diluting the sample 104 to a dilution ratio between about 1:1 to about 1:10. In another embodiment, diluting the sample 104 with the dilutive solution 110 can involve diluting the sample 104 to a dilution ratio between about 1:10 to about 1:100. In yet another embodiment, diluting the sample 104 with the dilutive solution 110 can involve diluting the sample 104 to a dilution ratio between about 1:100 to about 1:1000. In a further embodiment, diluting the sample 104 with the dilutive solution 110 can involve diluting the sample 104 to a dilution ratio between about 1:1000 to about 1:10000. Although FIG. 5 illustrates one reaction vessel 106 or one aliquot of the sample 104 being diluted, it is contemplated by this disclosure that multiple aliquots of the sample 104 can be diluted to different dilution ratios such that one or more diluted samples 112 can act as internal controls.

As will be discussed in the following sections in relation to FIG. 6, in alternative embodiments, the method 500 can comprise diluting the sample 104 comprising the infectious agent 102 with deionized water, a saline solution, or a combination thereof serving as the dilutive solution 110. In these embodiments, the diluted sample(s) 112 can be introduced to one or more sensors through sample delivery conduits comprising growth media/growth inducers and anti-infectives such that the diluted sample 112 is mixed with the growth media/growth inducers and anti-infectives. More details concerning these embodiments will be discussed in the following sections.

The method 500 can further comprise separating the diluted sample 112 into multiple aliquots such as, for example, a first aliquot and a second aliquot in step 5C. The method 500 can also comprise introducing and mixing an anti-infective 502 at a first concentration into the first aliquot of the diluted sample 112. The mixture comprising the first aliquot and the anti-infective 502 at the first concentration can be referred to as a test solution 506. The second aliquot of the diluted sample 112 without the anti-infective 502 can be used as a control solution 504. Although FIG. 5 illustrates only one test solution 506 comprising the first aliquot and the anti-infective 502, it is contemplated by this disclosure and should be understood by one of ordinary skill in the art that the method 500 and systems disclosed herein can assay multiple test solutions and some such test solutions can comprise a different anti-infective 502, the same anti-infective 502 at a different concentration, or a different anti-infective 502 at a different concentration. For example, the anti-infective 502 can be diluted to two different concentrations before being introduced to two different reaction vessels 106 containing aliquots of the diluted sample 112.

The anti-infective 502 used in the systems and methods disclosed herein can comprise a bacteriostatic anti-infective, a bactericidal anti-infective, an anti-fungal anti-infective, or a combination thereof.

In certain embodiments, the bacteriostatic anti-infective can comprise β-lactams (including but not limited to penicillins such as ampicillin, amoxicillin, flucloxacillin, penicillin, amoxicillin/clavulanate, and ticarcillin/clavulanate and monobactams such as aztreonam), β-lactam and β-lactam inhibitor combinations (including but not limited to piperacillin-tazobactam and ampicillin-sulbactam), Aminoglycosides (including but not limited to amikacin, gentamicin, kanamycin, neomycin, netilmicin, paromomycin, streptomycin, spectinomycin, and tobramycin), Ansamycins (including but not limited to rifaximin), Carbapenems (including but not limited to ertapenem, doripenem, imipenem, and meropenem), Cephalosporins (including but not limited to ceftaroline, cefepime, ceftazidime, ceftriaxone, cefadroxil, cefalotin, cefazolin, cephalexin, cefaclor, cefprozil, fecluroxime, cefixime, cefdinir, cefditoren, cefotaxime, cefpodoxime, ceftibuten, and ceftobiprole), Chloramphenicols, Glycopeptides (including but not limited to vancomycin, teicoplanin, telavancin, dalbavancin, and oritavancin), Folate Synthesis Inhibitors (including but not limited to trimethoprim-sulfamethoxazole), Fluoroquinolones (including but not limited to ciprofloxacin), Lincosamides (including but not limited to clindamycin, lincomycin, azithromycin, clarithromycin, dirithromycin, roxithromycin, telithromycin, and spiramycin), Lincosamines, Lipopeptides, Macrolides (including but not limited to erythromycin), Monobactams, Nitrofurans (including but not limited to furazolidone and nitrofurantoin), Oxazolidinones (including but not limited to linezolid, posizolid, radezolid, and torezolid), Quinolones (including but not limited to enoxacin, gatifloxacin, gemifloxacin, levofloxacin, lomefloxacin, moxifloxacin, naldixic acid, norfloxacin, trovafloxacin, grepafloxacin, sparfloxacin, and temafloxacin), Rifampins, Streptogramins, Sulfonamides (including but not limited to mafenide, sulfacetamide, sulfadiazine, sulfadimethoxine, sulfamethizole, sulfamethoxazole, sulfasalazine, and sulfisoxazole), Tetracyclines (including but not limited to oxycycline, minocycline, demeclocycline, doxycycline, oxytetracycline, and tetracycline), polypeptides (including but not limited to bacitracin, polymyxin B, colistin, and cyclic lipopeptides such as daptomycin), phages, or a combination or derivative thereof.

In other embodiments, the anti-infective 502 can comprise clofazimine, ethambutol, isoniazid, rifampicin, arsphenamine, chloramphenicol, fosfomycin, metronidazole, tigecycline, trimethoprim, or a combination or derivative thereof.

In certain embodiments, the anti-fungal can comprise Amphotericin B, Anidulafungin, Caspofungin, Fluconazole, Flucytosine, Itraconazole, Ketoconazole, Micafungin, Posaconazole, Ravuconazole, Voriconazole, or a combination or derivative thereof.

The method 500 can also comprise incubating the first aliquot and the second aliquot at an elevated temperature for a period of time in step 5E. The first aliquot and the second aliquot can be incubated in their respective reaction vessels 106 or transferred to different reaction vessels 106 or containers. For example, the first aliquot and the second aliquot can be heated to a temperature of between about 30° C. and about 40° C. (e.g., 35° C.±2° C.) and allowed to incubate for an incubation period 114. The incubation period 114 can range from 15 minutes to over one hour. In other embodiments, the incubation period 114 can be less than 15 minutes or up to 48 hours.

The incubation period 114 can be adjusted based on the type of infectious agent 102 suspected in the sample 104, such as the type of bacteria or fungus. The incubation period 114 can also be adjusted based on the type of anti-infective 502, the mechanism of action of the anti-infective 502, the amount of the sample 104, or a combination thereof. The incubation period 114 can be start-delayed or a pre-incubation time period can be added before the start of the incubation period 114. The start-delay or the pre-incubation time period can be added for slower acting drugs or anti-infectives 502 (e.g., β-lactams). In some embodiments, the start-delay or the pre-incubation time period can be between 10 minutes and 2 hours. In other embodiments, the start-delay or the pre-incubation time period can be as long as needed for the drug or anti-infective 502 to take effect. During the start-delay or pre-incubation time period, readings or measurements from the sensor(s) would not be used or would not be included as part of any growth curves generated (ORP signals monitored). The start-delay or the pre-incubation time period is particularly useful for instances where higher inoculums or a higher concentration of infectious agents 102 is present in the sample 104 or aliquots and where the signal is generated relatively fast in comparison to the mode of action of the drug or anti-infective 502.

The method 500 can further comprise introducing the test solution 506 to a first sensor 508 or exposing the first sensor 508 to the test solution 506 such that the test solution 506 is in fluid communication with a redox-active material of the first sensor 508 in step 5F(i). The method 500 can also comprise introducing the control solution 504 to a second sensor 510 or exposing the second sensor 510 to the control solution 504 such that the control solution 504 is in fluid communication with the redox-active material of the second sensor 510 in step 5F(ii).

In certain embodiments, the first sensor 508 and the second sensor 510 can be oxidation reduction potential (ORP) sensors configured to respond to a change in a solution characteristic (e.g., the ORP) of a measured solution. In the example embodiment shown in FIG. 5, exposing the first sensor 508 and the second sensor 510 to the test solution 506 and the control solution 504, respectively, can involve directly immersing at least part of a handheld or probe instance of the first sensor 508 and the second sensor 510 into the test solution 506 and the control solution 504, respectively. In this embodiment, the handheld or probe instance of the first sensor 508 or the second sensor 510 can be a handheld OPR sensor coupled to a standalone parameter analyzer 118 such as a voltmeter or multimeter. In alternative example embodiments also shown in FIG. 5, introducing the test solution 506 and the control solution 504 to the first sensor 508 and the second sensor 510, respectively, can involve injecting, delivering, or otherwise introducing the test solution 506 to a well or container comprising the first sensor 508 and introducing the control solution 504 to another well or container comprising the second sensor 510. In these embodiments, the first sensor 508 and the second sensor 510 can be fabricated on one substrate 202 or different substrates 202.

The substrate 202 can be comprised of a polymeric material, a metal, a ceramic, a semiconductor layer, an oxide layer, an insulator, or a combination thereof. The substrate 202 can be part of a test strip, cartridge, chip or lab-on-a-chip, microfluidic device, multi-well container, or a combination thereof. In some embodiments, the one or more parameter analyzers 118 can also be fabricated or located on the substrate 202. In other embodiments, the one or more parameter analyzers 118 can be standalone devices such as a voltmeter or a multimeter electrically coupled to the sensors.

As will be discussed in more detail in the following sections, each of the first sensor 508 and the second sensor 510 can comprise an active electrode and a reference electrode. In addition, the redox-active material 908 can comprise a gold layer, a platinum layer, a metal oxide layer, a carbon layer, or a combination thereof.

The method 500 can further comprise monitoring the ORP of the test solution 506 over a period of time using one or more parameter analyzers 118 coupled to the first sensor 508 in step 5F(i). The method 500 can also comprise monitoring the ORP of the control solution 504 over a similar period of time using one or more parameter analyzers 118 coupled to the second sensor 510 in step 5F(ii). In one or more embodiments, the ORPs of the test solution 506 and the control solution 504 can be monitored in the absence of any added or exogenous reporter molecules present in the test solution 506 or the control solution 504.

The test solution 506 and the control solution 504 can each have a solution characteristic. The solution characteristic of the test solution 506 and the solution characteristic of the control solution 504 can change as the amount of electro-active redox species changes due to the energy use, oxygen uptake or release, growth, or lack thereof of the infectious agents 102 in the test solution 506 and the control solution 504. For example, the amount of electro-active redox species in the test solution 506 can change as a result of increasing or diminishing cellular activity undertaken by the infectious agents 102 in the test solution 506. Also, for example, the amount of electro-active redox species in the control solution 504 can change as a result of cellular activity undertaken by the infectious agents 102 in the control solution 504. As a more specific example, the amount of electron donors from Table 1 (e.g., the amount of energy carriers such as nicotinamide adenine dinucleotide (NADH) and flavin adenine dinucleotide ($FADH_2$)) in the test solution 506 or the control solution 504 can change due to the growth or lack thereof of the infectious agents 102 in the test solution 506 or the control solution 504. Also, as another more specific example, the amount of oxygen depleted in the test solution 506 or the control solution 504 due to aerobic respiration can change due to the growth or lack thereof of the infectious agents 102 in the test solution 506 or the control solution 504.

The method 500 can further comprise comparing the ORP of the test solution 506 with the ORP of the control solution 504 to determine the susceptibility of the infectious agent 102 to the anti-infective 502 in step 5G. In some embodiments, comparing the ORP of the test solution 506 with the ORP of the control solution 504 can be done using one or more parameter analyzers 118 coupled to the first sensor 508, the second sensor 510, or a combination thereof. In other embodiments, comparing the ORP of the test solution 506 with the ORP of the control solution 504 can be done using another device electrically or communicatively coupled to the parameter analyzer 118 such as the reader 120. In yet additional embodiments, comparing the ORP of the test solution 506 with the ORP of the control solution 504 can be done using a combination of one or more parameter analyzers 118 and the reader 120.

In certain embodiments, the reader 120 can be a mobile device, a handheld device, a tablet device, or a computing device such as a laptop or desktop computer having a display 122. For example, the display 122 can be a mobile device display, a handheld device display, a tablet display, or a laptop or desktop monitor. In some embodiments, the parameter analyzer 118 can also comprise a display or can wirelessly communicate a signal or readout to a device having a display.

The parameter analyzer 118, the reader 120, or a combination thereof can monitor and compare the ORP of the test solution 506 with the ORP of the control solution 504 over a period of time. The period of time can be referred to as a detection window 512. The parameter analyzer 118, the reader 120, or a combination thereof can assess the susceptibility of the infectious agent 102 to the anti-infective 502 within this detection window 512. In one embodiment, the detection window 512 can be between 60 minutes and 120 minutes. In other embodiments, the detection window 512 can be between 5 minutes and 60 minutes. In additional embodiments, the detection window 512 can be greater than 120 minutes.

In one embodiment, the parameter analyzer 118, the reader 120, or a combination thereof can comprise one or more controllers or processors to execute logical commands concerning the comparison of the ORP of the test solution 506 with the ORP of the control solution 504. In this and other embodiments, the parameter analyzer 118, the reader 120, or a combination thereof can generate or instruct another device to generate a read-out, graph, or signal concerning a result of the comparison on a display such as the display 122.

For example, the parameter analyzer 118, the reader 120, or a combination thereof can determine or assess the susceptibility of the infectious agent 102 in the sample 104 as resistant to an anti-infective 502 when the parameter analyzer 118, the reader 120, or a combination thereof fails to detect a statistically significant difference between the ORP of the test solution 506 and the ORP of the control solution 504. This statistically significant difference can be a difference exceeding a threshold value or range. Conversely, the parameter analyzer 118, the reader 120, or a combination thereof can determine or assess the susceptibility of the infectious agent 102 as susceptible to an anti-infective 502 when the parameter analyzer 118, the reader 120, or a combination thereof detects certain statistically significant differences between the ORP of the test solution 506 and the ORP of the control solution 504 within the detection window 512.

Although not shown in FIG. 5, the method 500 can also comprise separating the diluted sample 112 into a third aliquot and introducing the anti-infective 502 at a second concentration into the third aliquot to form another test solution. In some embodiments, the second concentration of the anti-infective 502 can be less than the first concentration of the anti-infective 502 added to the first aliquot. In these embodiments, the second concentration of the anti-infective 502 can be obtained by diluting the first concentration of the anti-infective 502. In other embodiments, the second concentration can be greater than the first concentration.

The method 500 can further comprise introducing the other test solution to a third sensor such that the other test solution is in fluid communication with the redox-active material of the third sensor. The ORP of the other test solution 506 can be monitored over a period of time using one or more parameter analyzers 118 coupled to the third sensor. The ORP can be monitored in the absence of any added reporter molecules in the other test solution. The method 500 can also comprise comparing the ORP of the other test solution with the ORPs of the test solution 506 formed from the first aliquot and the control solution 504. The ORPs can be compared to determine a degree of susceptibility of the infectious agent 102 to the anti-infective 502. For example, the parameter analyzer 118, the reader 120, or a combination thereof can assess the degree or level of susceptibility of the infectious agent 102 in the sample 104 on a tiered scale. As a more specific example, the parameter analyzer 118, the reader 120, or a combination thereof can assess the susceptibility of the infectious agent 102 in the sample 104 as being resistant, of intermediate susceptibility, or susceptible to the anti-infective 502 based on a comparison of the ORPs of the two test solutions with each other and comparisons of the ORPs of the two test solutions with the control solution 504.

In some embodiments, one or more of the aforementioned steps of the method 500 can be stored as machine-executable instructions or logical commands in a non-transitory machine-readable medium (e.g., a memory or storage unit) of the parameter analyzer 118, the reader 120, or another device communicatively or electrically coupled to the parameter analyzer 118 or the reader 120. Any of the parameter analyzer 118, the reader 120, or another device coupled to the parameter analyzer 118 or the reader 120 can comprise one or more processors or controllers configured to execute the aforementioned instructions or logical commands.

The steps depicted in FIG. 5 do not require the particular order shown to achieve the desired result. Moreover, certain steps or processes may be omitted or occur in parallel in order to achieve the desired result. In addition, any of the systems or devices disclosed herein can be used in lieu of devices or systems shown in the steps of FIG. 5.

Figure 6:
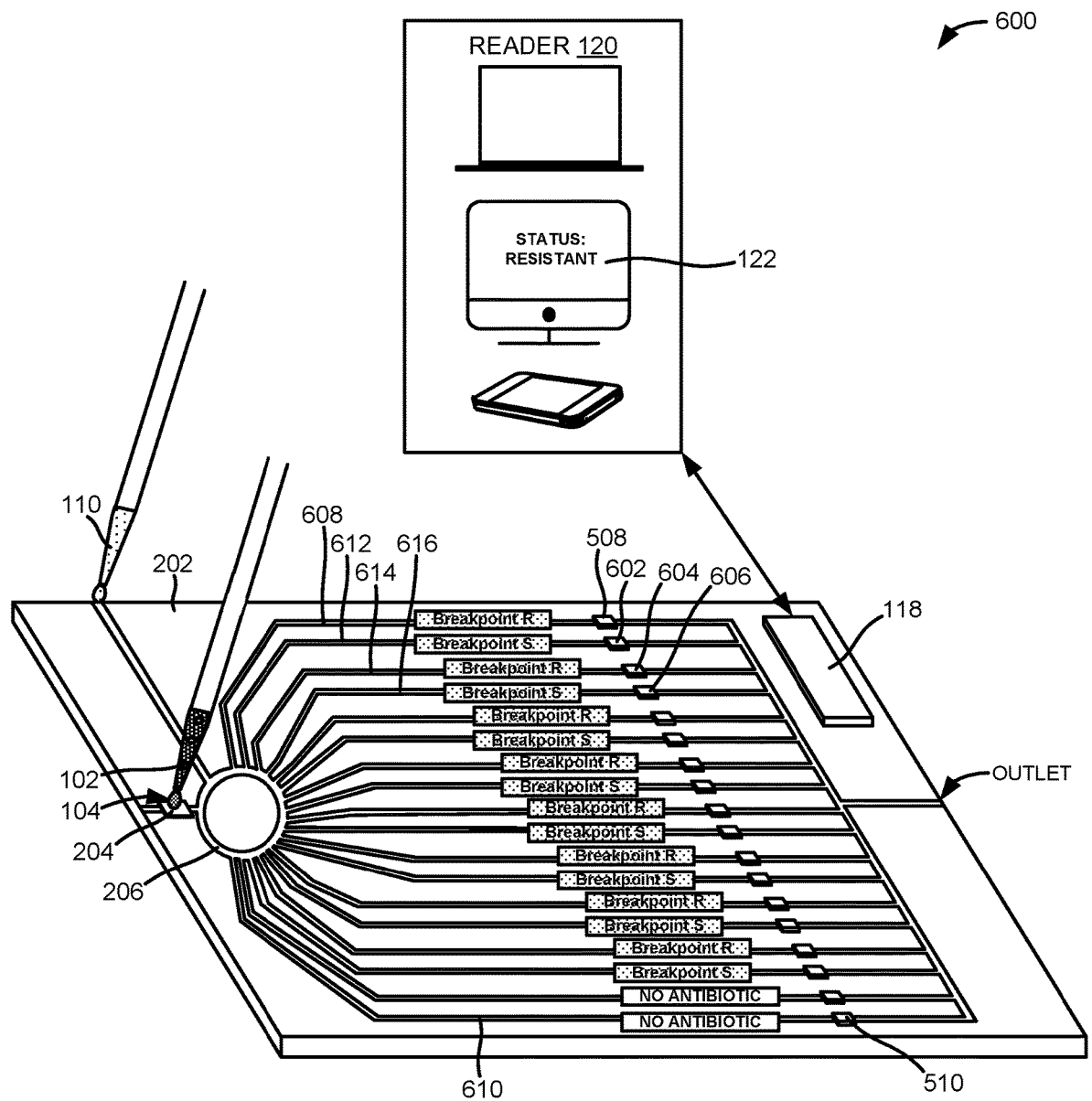
FIG. 6 illustrates one embodiment of a multiplex system for determining the susceptibility of one or more infectious agents to one or more anti-infectives.

FIG. 6 illustrates an embodiment of a multiplex system 600 for determining a susceptibility an infectious agent 102 as well as a level of susceptibility of an infectious agent 102 to one or more anti-infectives 502. In some embodiments, the multiplex system 600 can be part of a cartridge, a test strip, an integrated circuit, a micro-electro-mechanical system (MEMS) device, a microfluidic system or chip, or a combination thereof.

The system 600 can be another embodiment of the system 200 illustrated in FIG. 2C with many of the same components as the system 200. The system 600 can comprise the same sample delivery surface 204 defined on the same substrate 202. In one or more embodiments, the sample receiving surface 204 can be a flat surface for receiving the sample 104. In other embodiments, the sample receiving surface 204 can be a concave or tapered surface of a well, divot, dish, or container. For example, the sample 104 can be injected, pipetted, pumped, spotted, or otherwise introduced to the sample receiving surface 204 for analysis.

The system 600 can also comprise the one or more metering conduits 206 in fluid communication with the sample receiving surface 204. In some embodiments, the one or more metering conduits 206 can be channels, passageways, capillaries, tubes, parts therein, or combinations thereof for delivering the dilutive solution 110 to the sample 104 on the sample receiving surface 204. For example, the one or more metering conduits 206 can refer to channels, passageways, capillaries, or tubes defined on the substrate 202. Also, for example, the one or more metering conduits 206 can refer to channels, passageways, capillaries, or tubes serving as part of hydraulic pump, a pneumatic pump, peristaltic pump, a vacuum or positive pressure pump, a manual or mechanical pump, a syringe pump, or a combination thereof. For example, the one or more metering conduits 206 can be microfluidic channels or tubes or channels serving as part of a vacuum system.

In some embodiments, the one or more metering conduits 206 can be configured to dilute the sample 104 with the dilutive solution 110 to a dilution ratio between about 1:1 to about 1:10. In other embodiments, the one or more metering conduits 206 can be configured to dilute the sample 104 with the dilutive solution 110 to a dilution ratio between about 1:10 to about 1:100. In additional embodiments, the one or more metering conduits 206 can be configured to dilute the sample 104 with the dilutive solution 110 to a dilution ratio between about 1:100 to about 1:1000. In yet additional embodiments, the one or more metering conduits 206 can be configured to dilute the sample 104 with the dilutive solution 110 to a dilution ratio between about 1:1000 to about 1:10000.

The system 600 can also comprise a plurality of sensors and a plurality of sample delivery conduits connecting and extending in between each of the sensors and the sample receiving surface 204, the one or more metering conduits 206, or a combination thereof. In certain embodiments, the one or more metering conduits 206 can also separate the diluted sample into multiple aliquots including at least a first aliquot, a second aliquot, a third aliquot, a fourth aliquot, and a fifth aliquot. In these embodiments, aliquots of the diluted sample can automatically flow from the one or more metering conduits 206 into the sample delivery conduits leading to the sensors.

In other embodiments, the sample 104 can be diluted by a user or technician in a separate reaction vessel, test tube, or container. In these embodiments, the user can separate the diluted sample into multiple aliquots and introduce each of the aliquots to either the sample delivery conduits or the sensors directly.

In the example embodiment shown in FIG. 6, the plurality of sensors can comprise at least the first sensor 508, the second sensor 510, a third sensor 602, a fourth sensor 604, and a fifth sensor 606. Although five sensors are described herein it should be understood by one of ordinary skill in the art that the system 600 can comprise more than five sensors.

In some embodiments, the sensors (including any of the first sensor 508, the second sensor 510, the third sensor 602, the fourth sensor 604, and the fifth sensor 606) can be the sensors 900 described in connection with FIGS. 9A and 9B. For example, the sensors can be micro- or nano-scale ORP sensors. The sensors can be fabricated or located on a surface of the substrate 202. For example, the substrate 202 can be part of a circuit, chip, or device and the sensors can comprise components of such circuits, chips, or devices including, but not limited to, one or more transistors, gates, or other electrical components. In some embodiments, the sensors can be positioned within a well, divot, cut-out, or groove defined along the substrate 202. In these and other embodiments, the diluted samples can be injected, directed, or otherwise introduced into each of the wells, divots, cut-outs, or grooves.

Each of the sensors can comprise an active electrode and a reference electrode. Each of the sensors can also comprise a redox-active material 908 (see FIGS. 9A and 9B) or layer such as a gold layer, a platinum layer, a metal oxide layer, carbon layer, or a combination thereof. The sensors will be discussed in more detail in the following sections.

The sample delivery conduits (e.g., the first sample delivery conduit 608, the second sample delivery conduit 610, the third sample delivery conduit 612, the fourth sample delivery conduit 614, and the fifth sample delivery conduit 616) can extend in between the sample receiving surface 204 and the plurality of sensors or extend in between the one or more metering conduits 206 and the plurality of sensors. The sample delivery conduits can be channels, passageways, capillaries, tubes, microfluidic channels, parts therein, or combinations thereof for delivering the diluted sample to the sensors. The sample delivery conduits can allow aliquots of the diluted sample to be in fluid communication the sensors. For example, each of the sample delivery conduits can allow an aliquot of the diluted ample to be in fluid communication with a redox-active material or layer of a sensor.

In the example embodiment shown in FIG. 6, each of the sample delivery conduits can be covered or coated by a lyophilized or dried form of an anti-infective. The anti-infective can be any of the anti-infectives 502 discussed in connection with FIG. 5. The sample delivery conduits can be configured such that aliquots of the diluted sample flow through the sample delivery conduits and mix with the lyophilized or dried forms of the anti-infective en route to the sensors. In this and other example embodiments, the dilutive solution 110 used to dilute the sample 104 can comprise growth media such as Mueller Hinton growth media (MHG), a growth inducer, or a combination thereof.

In other embodiments, the dilutive solution 110 used to dilute the sample 104 can be deionized water or saline solution and the sample delivery conduits 208 can be covered or coated by both a lyophilized or dried form of the anti-infective and a lyophilized or dried form of the growth media. In these embodiments, aliquots of the diluted sample flowing through the sample delivery conduits can mix with the lyophilized or dried forms of the anti-infective and the growth media en route to the sensors.

In additional embodiments not shown in FIG. 6, the sample delivery conduits 208 can contain anti-infectives, growth media, or a combination thereof in aqueous form. In these embodiments, aliquots of the diluted sample can mix with the aqueous forms of the anti-infective, the growth media, or a combination thereof en route to the sensors.

In yet additional embodiments, some of the sensors themselves (e.g., one or more layers of the sensor) can be covered or coated by lyophilized or dried forms of the anti-infective, the growth media, or a combination thereof. In these embodiments, aliquots of the diluted sample can mix with the anti-infective, the growth media, or a combination thereof when the aliquots reach or are in fluid communication with the sensors. Moreover, in other embodiments not shown in the figures, a surface in the vicinity of the sensors can be covered or coated by lyophilized or dried forms of the anti-infective, the growth media, or a combination thereof. In these embodiments, aliquots of the diluted sample can mix with the lyophilized or dried forms of the anti-infective, the growth media, or a combination thereof when the diluted sample is in fluid communication with the surface covered or coated by the lyophilized anti-infective or growth media.

In all such embodiments, at least one of the sample delivery conduits leading up to at least one of the sensors can be free or devoid of anti-infectives. In these embodiments, the diluted sample flowing through this sample delivery conduit can act as a control solution. Also, in these embodiments, each of the aliquots of the diluted sample mixed with the anti-infective can be referred to as a test solution.

The system 600 shown in FIG. 6 can be used to determine the susceptibility of a sample 104 comprising the infectious agent 102 to multiple anti-infectives (as well as multiple concentrations of one or more anti-infectives) concurrently. As such, one benefit of the multiplex system 600 of FIG. 6 is the ability to perform high-throughput antibiotic susceptibility testing.

In further alternative embodiments not shown in the figures, a user can dilute the sample 104 with growth media and mix one or more anti-infectives into aliquots of the diluted sample prior to introducing the mixture to the system 600. In these embodiments, the user can introduce the mixture comprising the diluted sample and the anti-infectives to the sample receiving surface 204 or the sensors directly.

In some embodiments, the system 600 can further comprise an incubating component configured to incubate the diluted sample mixed with the anti-infective, the growth media, or a combination thereof by heating the mixture to a temperature of between about 30° C. and about 40° C. (e.g., 35° C.±2° C.) for a period of time (e.g., the incubation period 114).

The system 600 can also comprise one or more parameter analyzers 118 electrically or communicatively coupled to the sensors and a reader 120 electrically or communicatively coupled to the one or more parameter analyzers 118. In some embodiments, the one or more parameter analyzers 118 can be fabricated or located on the substrate 202. In other embodiments, the one or more parameter analyzers 118 can be standalone devices such as a voltmeter or a multimeter electrically coupled to the sensor. In some embodiments, the reader 120 and the parameter analyzer(s) 118 can be integrated into one device. The parameter analyzer 118 and the reader 120 depicted in FIG. 6 can be the same parameter analyzers 118 and reader 120 depicted in FIG. 5.

The parameter analyzer 118, the reader 120, or a combination thereof can monitor and compare the ORP of the test solution with the ORP of one or more control solutions over a period of time. This period of time can be between 60 minutes and 120 minutes. In other embodiments, this period of time can be between 5 minutes and 60 minutes. In additional embodiments, this period of time can be greater than 120 minutes.

In some embodiments, the parameter analyzer 118, the reader 120, or a combination thereof can comprise one or more controllers or processors to execute logical commands concerning the comparison of the ORPs of the test solutions with the ORP of the control solution. In this and other embodiments, the parameter analyzer 118, the reader 120, or a combination thereof can generate or instruct another device to generate a read-out, graph, or signal concerning a result of the comparison on a display such as the display 122.

For example, the parameter analyzer 118, the reader 120, or a combination thereof can determine or assess the susceptibility of the infectious agent 102 in the sample 104 as resistant to an anti-infective when the parameter analyzer 118, the reader 120, or a combination thereof fails to detect a statistically significant difference between the ORP of one of the test solutions and the ORP of the control solution. This statistically significant difference can be a difference exceeding a threshold value or range. Conversely, the parameter analyzer 118, the reader 120, or a combination thereof can determine or assess the susceptibility of the infectious agent 102 as susceptible to an anti-infective when the parameter analyzer 118, the reader 120, or a combination thereof detects certain statistically significant differences between the ORP of one of the test solutions and the ORP of the control solution.

As will be discussed in the following sections, the system 600 can also assess the degree or level of susceptibility of the infectious agent 102 in the sample 104 on a tiered scale. As a more specific example, the parameter analyzer 118, the reader 120, or a combination thereof can assess the susceptibility of the infectious agent 102 in the sample 104 as being resistant, of intermediate susceptibility, or susceptible to the anti-infective 502 based on a comparison of the ORPs of two test solutions with each other and comparisons of the ORPs of the two test solutions with the control solution 504.

For example, as shown in FIG. 6, the system 600 can comprise at least a first sample delivery conduit 608, a second sample delivery conduit 610, a third sample delivery conduit 612, a fourth sample delivery conduit 614, and a fifth sample delivery conduit 616. The metering conduit 206 can also separate the diluted sample into a first aliquot, a second aliquot, a third aliquot, a fourth aliquot, and a fifth aliquot. The system 600 can direct the first aliquot to the first sample delivery conduit 608, the second aliquot to the second sample delivery conduit 610, the third aliquot to the third sample delivery conduit 612, the fourth aliquot to the fourth sample delivery conduit 614, and the fifth aliquot to the fifth sample delivery conduit 616.

The first sample delivery conduit 608 can comprise a first anti-infective at a first concentration and the third sample delivery conduit 612 can comprise the first anti-infective at a second concentration. In some embodiments, the second concentration can be less than the first concentration and can be obtained by diluting a solution comprising the first anti-infective at the first concentration.

The fourth sample delivery conduit 614 can comprise a second anti-infective at a first concentration and the fifth sample delivery conduit 616 can comprise the second anti-infective at a second concentration. The second anti-infective can be a different anti-infective than the first anti-infective.

The second sample delivery conduit 610 can be free or devoid of any anti-infective such that the second aliquot of the diluted sample introduced through the second sample delivery conduit 610 can be considered a control solution. The first sample delivery conduit 608 can be configured to introduce the first aliquot of the diluted sample to the first sensor 508. The first aliquot can mix with the lyophilized or dried first anti-infective at the first concentration to form a first test solution. The third sample delivery conduit 612 can be configured to introduce the third aliquot of the diluted sample to the third sensor 602. The third aliquot can mix with the lyophilized or dried first anti-infective at the second concentration to form a second test solution. The fourth sample delivery conduit 614 can be configured to introduce the fourth aliquot of the diluted sample to the fourth sensor 604. The fourth aliquot can mix with the lyophilized or dried second anti-infective at the first concentration to form a third test solution. The fifth sample delivery conduit 616 can be configured to introduce the fifth aliquot of the diluted sample to the fifth sensor 606. The fifth aliquot can mix with the lyophilized or dried second anti-infective at the second concentration to form a fourth test solution.

The parameter analyzer 118, the reader 120, or a combination thereof can monitor the ORP of the first test solution when the first test solution is in fluid communication with the redox-active material of the first sensor 508. The parameter analyzer 118, the reader 120, or a combination thereof can monitor the ORP of the control solution when the control solution is in fluid communication with the redox-active material of the second sensor 510. The parameter analyzer 118, the reader 120, or a combination thereof can monitor the ORP of the second test solution when the second test solution is in fluid communication with the redox-active material of the third sensor 602. The parameter analyzer 118, the reader 120, or a combination thereof can monitor the ORP of the third test solution when the third test solution is in fluid communication with the redox-active material of the fourth sensor 604. The parameter analyzer 118, the reader 120, or a combination thereof can monitor the ORP of the fourth test solution when the fourth test solution is in fluid communication with the redox-active material of the fifth sensor 606. The ORPs of the first test solution, the second test solution, the third test solution, the fourth test solution, and the control solution can be monitored in the absence of any added reporter or exogenous reporter molecules in the first test solution, the second test solution, the third test solution, the fourth test solution, and the control solution, respectively.

The parameter analyzer 118, the reader 120, or a combination thereof can compare the ORP of the second test solution with the ORPs of the first test solution and the control solution to determine a degree of susceptibility of the infectious agent 102 to the first anti-infective. For example, the parameter analyzer 118, the reader 120, or a combination thereof can determine the infectious agent 102 as susceptible to the first anti-infective when the parameter analyzer 118, the reader 120, or a combination thereof detects both a statistically significant difference between the ORP of the first test solution and the ORP of the control solution (i.e., the infectious agents 102 are dead or dying in the first test solution) and a statistically significant difference between the ORP of the second test solution and the ORP of the control solution (i.e., the infectious agents 102 are dead or dying in the second test solution). Alternatively, the parameter analyzer 118, the reader 120, or a combination thereof can determine the infectious agent 102 as resistant to the first anti-infective when the parameter analyzer 118, the reader 120, or a combination thereof fails to detect a statistically significant difference between the ORP of the first test solution and the ORP of the control solution (i.e., the infectious agents 102 are alive and growing in the first test solution) and fails to detect a statistically significant difference between the ORP of the second test solution and the ORP of the control solution (i.e., the infectious agents 102 are alive and growing in the second test solution). As a further alternative example, the parameter analyzer 118, the reader 120, or a combination thereof can determine the infectious agent 102 as of intermediate susceptibility to the first anti-infective when the parameter analyzer 118, the reader 120, or a combination thereof detects a statistically significant difference between the ORP of the first test solution and the ORP of the control solution (i.e., the infectious agents 102 are dead or dying in the first test solution or the first anti-infective at a higher concentration) but fails to detect a statistically significant difference between the ORP of the second test solution and the ORP of the control solution (i.e., the infectious agents 102 are alive and growing in the second test solution or the first anti-infective at the lower concentration).

The parameter analyzer 118, the reader 120, or a combination thereof can also compare the ORP of the fourth test solution with the ORPs of the third test solution and the control solution to determine a degree of susceptibility of the infectious agent 102 to the second anti-infective. For example, the parameter analyzer 118, the reader 120, or a combination thereof can determine the infectious agent 102 as susceptible to the second anti-infective when the parameter analyzer 118, the reader 120, or a combination thereof detects both a statistically significant difference between the ORP of the third test solution and the ORP of the control solution (i.e., the infectious agents 102 are dead or dying in the third test solution (which is the second anti-infective at the higher concentration)) and a statistically significant difference between the ORP of the fourth test solution and the ORP of the control solution (i.e., the infectious agents 102 are dead or dying in the fourth test solution (which is the second anti-infective at the lower concentration)). Alternatively, the parameter analyzer 118, the reader 120, or a combination thereof can determine the infectious agent 102 as resistant to the second anti-infective when the parameter analyzer 118, the reader 120, or a combination thereof fails to detect a statistically significant difference between the ORP of the third test solution and the ORP of the control solution (i.e., the infectious agents 102 are alive and growing in the third test solution (which is the second anti-infective at the higher concentration)) and fails to detect a statistically significant difference between the ORP of the fourth test solution and the ORP of the control solution (i.e., the infectious agents 102 are alive and growing in the fourth test solution (which is the second anti-infective at the lower concentration)). Furthermore, the parameter analyzer 118, the reader 120, or a combination thereof can determine the infectious agent 102 as of intermediate susceptibility to the second anti-infective when the parameter analyzer 118, the reader 120, or a combination thereof detects a statistically significant difference between the ORP of the third test solution and the ORP of the control solution (i.e., the infectious agents 102 are dead or dying in the third test solution (which is the second anti-infective at the higher concentration)) but fails to detect a statistically significant difference between the ORP of the fourth test solution and the ORP of the control solution (i.e., the infectious agents 102 are alive and growing in the fourth test solution (which is the second anti-infective at the lower concentration)).

Figure 7A:
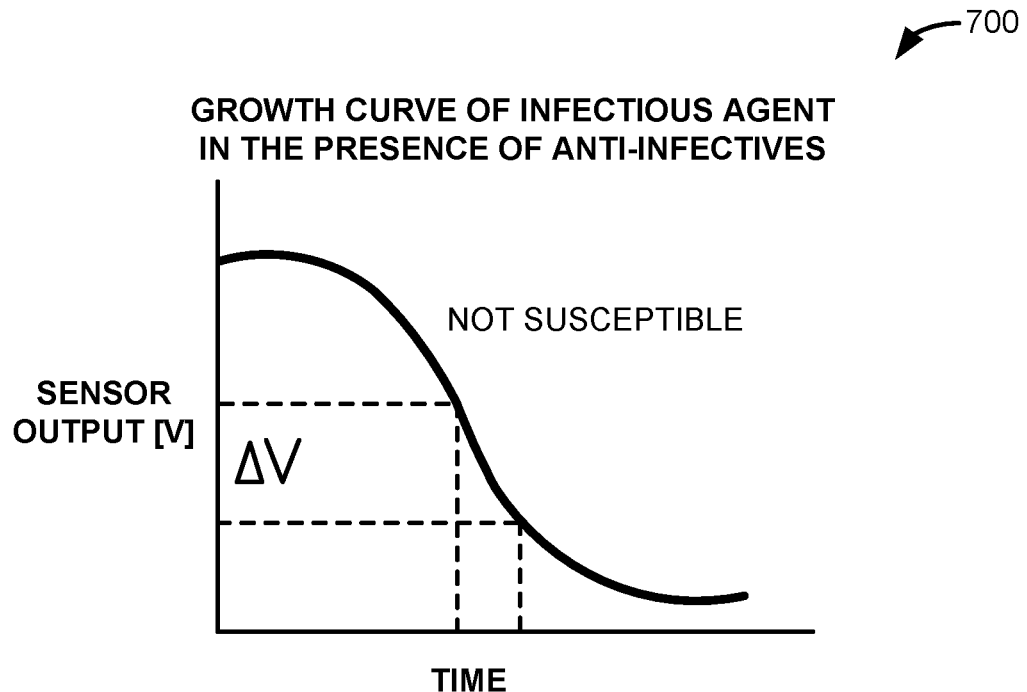
FIG. 7A illustrates a growth curve of an infectious agent resistant to one or more anti-infectives.

FIG. 7A illustrates an example growth curve 700 of an infectious agent 102 not susceptible or resistant to an anti-infective (such as anti-infective 502) in solution. The growth curve 700 can be recorded by monitoring the sensor output of an ORP sensor (including, but not limited to, the first sensor 508 or the second sensor 510) in fluid communication with the sampled solution. In one embodiment, the sensor output can be a potential difference between an active electrode and a reference electrode (see FIGS. 9A and 9B). The sensor output of the ORP sensor can change as the ORP of the sampled solution (e.g., any of the test solutions or the control solution 504) changes.

The voltage output of the ORP sensor can change over time. For example, as shown in FIG. 7A, the voltage output of the sensor can decrease over time as the solution characteristic of the sampled solution changes due to the energy use, oxygen uptake or release, growth, or metabolism of the infectious agents 102 in solution. In some embodiments, the change (e.g., decrease) in the voltage output of the sensor can follow a sigmoidal pattern or shape, a step function or shape, or other patterns or shapes. Over longer time scales, the sensor output or voltage can begin to increase or become more positive.

For example, the voltage output of the sensor can decrease over time as the solution characteristic of the sampled solution changes as a result of cellular activity undertaken by the infectious agents 102 in solution. As a more specific example, the solution characteristic of the sampled solution can change as the amount of energy carriers (such as nicotinamide adenine dinucleotide (NADH) and flavin adenine dinucleotide ($FADH_2$)) in the sampled solution changes due to the growth of anti-infective resistant infectious agents 102. Also, as another more specific example, the amount of oxygen depleted in the sampled solution can change due to the growth or lack thereof of the infectious agents 102 in solution.

Figure 7B:
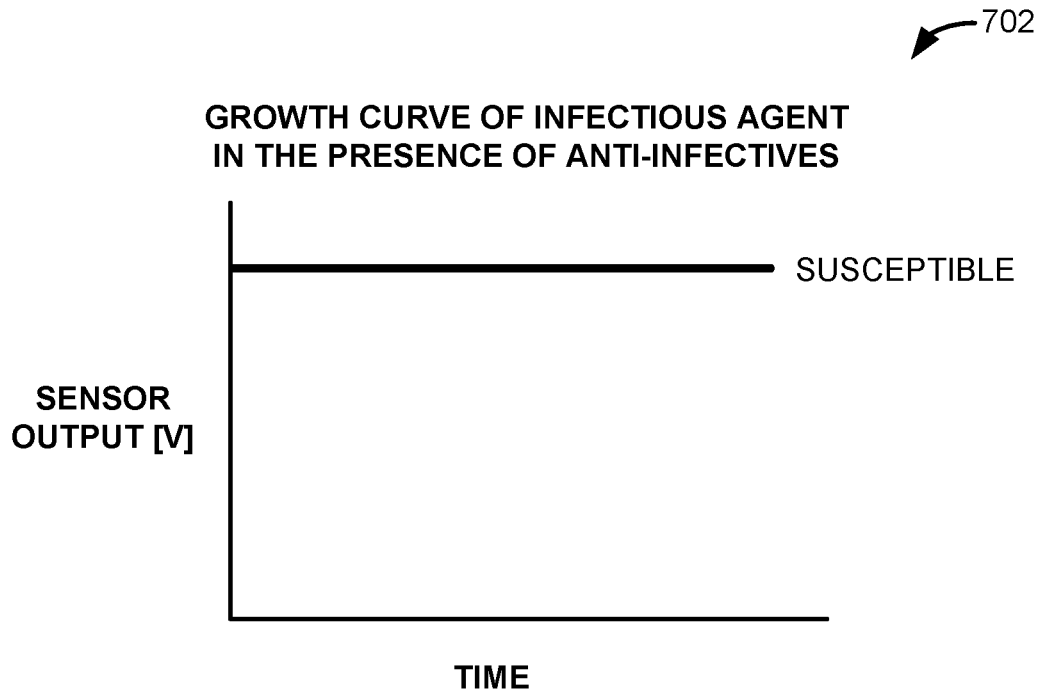
FIG. 7B illustrates a growth curve of an infectious agent susceptible to one or more anti-infectives.

FIG. 7B illustrates an example growth curve 702 of an infectious agent 102 susceptible to or not resistant to an anti-infective (such as anti-infective 502) in solution. The growth curve 702 can be recorded by monitoring the sensor output of an ORP sensor in fluid communication with the sampled solution. As shown in FIG. 7B, the growth curve 702 can be relatively constant (e.g., a substantially flat line) or change very little. In other embodiments not shown in FIG. 7B, the growth curve 702 can exhibit changes within a predetermined threshold range. The sensor output of the ORP sensor can stay relatively constant as the ORP of the sampled solution (e.g., any of the test solutions or the control solution 504) stays relatively constant.

In one embodiment, the voltage output of the ORP sensor can be a potential difference between an active electrode and a reference electrode such as the external reference electrode, the on-chip reference electrode, or another reference electrode.

The voltage output of the ORP sensor can stay relatively constant as the solution characteristic of the sampled solution stays relatively constant due to the inhibitive effects of the anti-infective 502 on the infectious agents 102 in solution.

Figure 8:
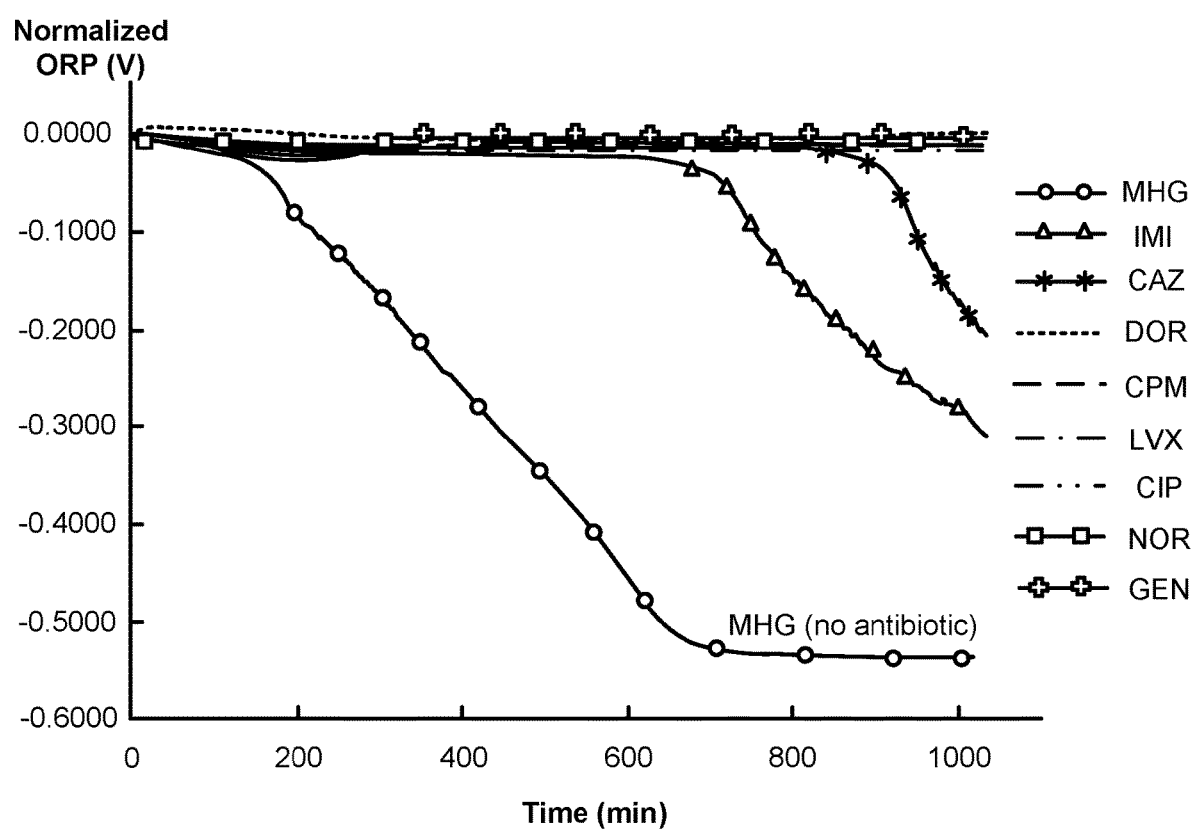
FIG. 8 illustrates growth curves of bacteria in the presence of certain anti-infectives.

FIG. 8 illustrates example growth curves of *Pseudomonas aeruginosa* (PAe) from positive blood culture in the presence of various anti-infectives 502. Blood culture positive for PAe was diluted into Mueller Hinton growth media (MHG) to a concentration of $5*10^5$ CFU/mL and probed with different antibiotics at their susceptibility breakpoints. As shown in FIG. 8, the antibiotics include (1) imipenem (IMI), (2) ceftazidime (CAZ), (3) doripenem (DOR), (4) cefepime (CPM), (5) levofloxacin (LVX), (6) ciprofloxacin (CIP), (7) norfloxacin (NOR), and (8) gentamicin (GEN). PAe and antibiotic mixtures were exposed to ORP sensors (for example, any of the sensors discussed in connection with FIGS. 5 and 6) and changes in the ORP of the mixture were assessed over time and compared to the bacterial sample without antibiotic (curve labeled MHG in FIG. 8). A flat or substantially flat line over the entire detection period can indicate elimination of the bacteria or susceptibility to the antibiotic. A flat or substantially flat line followed by a delayed change in ORP can indicate partial elimination of the bacteria (i.e., time-shifted regrowth in the presence of the antibiotic) or intermediate susceptibility to the antibiotic.

Figure 9A:
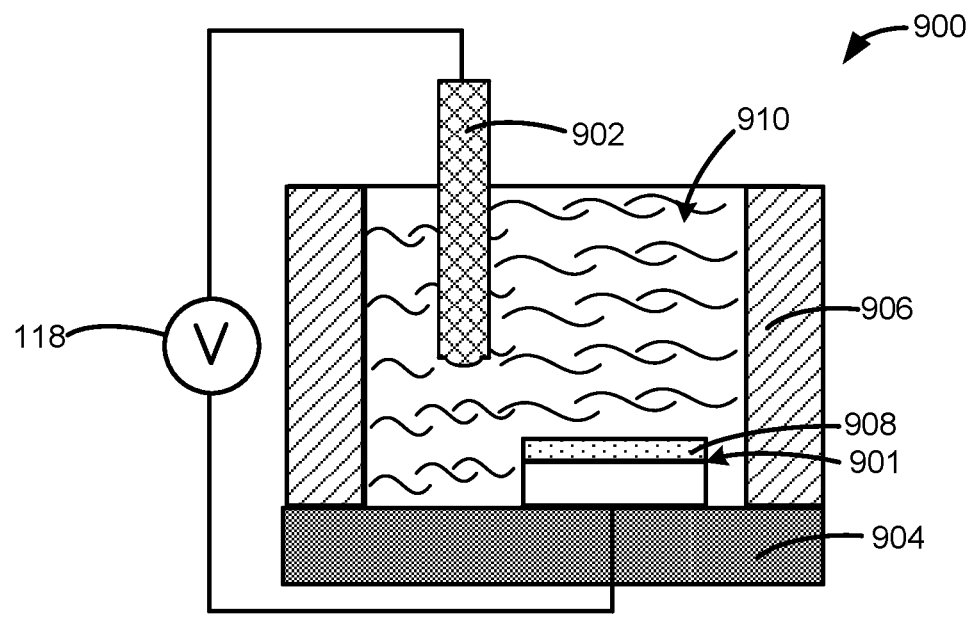
FIG. 9A illustrates a schematic of an embodiment of a sensor used as part of the methods and systems described herein.

FIG. 9A illustrates a side view of one embodiment of a sensor 900. The sensor 900 can be or refer to any of the sensors depicted in FIGS. 1, 2A, 2B, 2C, 5, and 6 (including but not limited to sensor 116 of FIG. 1, 2A, 2B, or 2C; the first sensor 508 or the second sensor 510 of FIG. 5 or 6; and the third sensor 602, the fourth sensor 604, or the fifth sensor 606 of FIG. 6). The sensor 900 can be an electrochemical cell comprising an active electrode 901 and an external reference electrode 902. In some embodiments of the sensor 900, the active electrode 901 and the external reference electrode 902 are the only electrodes of the sensor 900.

The active electrode 901 can extend from or be disposed on a substrate layer 904. The substrate layer 904 can be composed of, but is not limited to, any non-conducting material such as a polymer, an oxide, a ceramic, or a composite thereof. The electrochemical cell can be surrounded or contained by walls 906 configured to retain a sampled solution 910. The walls 906 can be made of an inert or non-conductive material.

The sampled solution 910 can refer to any of the diluted sample 112, the test solutions, the control solution 504, or an aliquot thereof. At least part of external reference electrode 902 can be in fluid communication or fluid contact with the sampled solution 910. For example, the external reference electrode 902 can extend into or be immersed in the sampled solution 910. The external reference electrode 902 can also have a stable or well-known internal voltage and the sensor 900 can use the external reference electrode 902 to determine or measure a relative change in the potential of the active electrode 901. In one embodiment, the external reference electrode 902 can be a standalone probe or electrode. In other embodiments, the external reference electrode 902 can be coupled to the parameter analyzer 118. In some embodiments, multiple sensors (including but not limited to any of the first sensor 508, the second sensor 510, the third sensor 602, the fourth sensor 604, or the fifth sensor 606) can share and use the same external reference electrode 902.

In one embodiment, the external reference electrode 902 can be a silver/silver chloride (Ag/AgCl) electrode. In other embodiments, the external reference electrode 902 can comprise a saturated calomel reference electrode (SCE) or a copper-copper (II) sulfate electrode (CSE). The external reference electrode 902 can also be a pseudo-reference electrode including any metal that is not part of the active electrode such as platinum, silver, gold, or a combination thereof; any metal oxide or semiconductor oxide material such as aluminum oxide, iridium oxide, silicon oxide; or any conductive polymer electrodes such as polypyrrole, polyaniline, polyacetylene, or a combination thereof.

The active electrode 901 can comprise multiple conductive layers (e.g., a stack of metallic layers) and a redox-active material 908 or layer such as a gold layer, a platinum layer, a metal oxide layer, a carbon layer, or a combination thereof on top of the multiple conductive layers. In some embodiments, the metal oxide layer can comprise an iridium oxide layer, a ruthenium oxide layer, or a combination thereof. The parameter analyzer 118 can be coupled to the active electrode 901 and the external reference electrode 902.

The parameter analyzer 118 can determine the ORP of the sampled solution 910 by measuring the potential difference between the external reference electrode 902 and the active electrode 901 instantly or over a period of time. As shown in FIG. 9A, the parameter analyzer 118 can be a voltmeter or any other type of high-impedance amplifier or sourcemeter. The voltmeter can measure a relative change in an equilibrium potential at an interface between the redox-active material 908 of the active electrode 901 and the sampled solution 910 containing electro-active redox species. The solution characteristic of the sampled solution 910 can change as the amount of electro-active redox species changes due to the energy use, oxygen uptake or release, growth, or metabolism of the infectious agents 102 in solution. For example, the amount of electro-active redox species in the sampled solution 910 can change as a result of cellular activity undertaken by the infectious agents 102 in solution. As a more specific example, the amount of electron donors from Table 1 (e.g., the amount of energy carriers such as nicotinamide adenine dinucleotide (NADH) and flavin adenine dinucleotide ($FADH_2$)) in the sampled solution 910 can change due to the growth or lack thereof of the infectious agents 102 in solution. Also, as another more specific example, the amount of oxygen depleted in the sampled solution 910 can change due to the growth or lack thereof of the infectious agents 102 in solution.

In one embodiment, the active electrode 901 can comprise a metallic layer. The metallic layer can comprise a gold layer, a platinum layer, or a combination thereof. The active electrode 901 can also comprise multiple layers comprising a semiconductor layer having a redox-active metal oxide layer, such as iridium oxide or ruthenium oxide on top of the multiple layers. In other embodiments, the active electrode 901 can comprise one or more metallic layers, one or more redox-active metal oxide layers, one or more semiconductor layers, or any combination or stacking arrangement thereof.

Figure 9B:
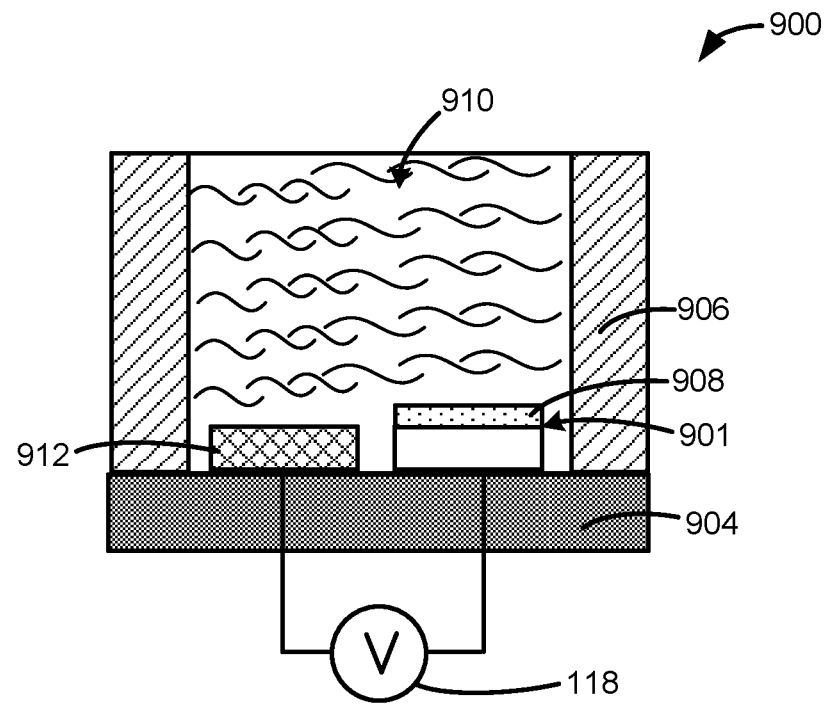
FIG. 9B illustrates a schematic of another embodiment of the sensor used as part of the methods and systems described herein.

FIG. 9B illustrates a side view of another embodiment of the sensor 900 having an on-chip reference electrode 912 disposed on the substrate layer 904 in lieu of the external reference electrode 902 of FIG. 9A. In some embodiments of the sensor 900, the active electrode 901 and the on-chip reference electrode 912 are the only electrodes of the sensor 900.

In these and other embodiments, the on-chip reference electrode 912 can be coated by a polymeric coating. For example, the on-chip reference electrode 912 can be coated by a polyvinyl chloride (PVC) coating, a perfluorosulfonate coating (e.g., Nafion™), or a combination thereof.

The on-chip reference electrode 912 can serve the same purpose as the external reference electrode 902 except be fabricated on or integrated with the substrate layer 904. The on-chip reference electrode 912 can be located adjacent to or near the active sensor 120. The sensor 900 of FIG. 9B can serve the same function as the sensor 900 of FIG. 9A. Similar to the active electrode 901 of FIG. 9B, the on-chip reference electrode 912 can also be in fluid communication or communication with the sampled solution 910 retained within walls 906.

The on-chip reference electrode 912 can be comprised of a metal, a semiconductor material, or a combination thereof. The metal of the on-chip reference electrode 912 can be covered by an oxide layer, a silane layer, a polymer layer, or a combination thereof. In another embodiment, the on-chip reference electrode 912 can be a metal combined with a metal salt such as an Ag/AgCl on-chip reference electrode. In another embodiment, the on-chip reference electrode can be a miniaturized electrode with a well-defined potential. In some embodiments, multiple sensors can share and use the same on-chip reference electrode 912. The on-chip reference electrode 912 can comprise a saturated calomel reference electrode (SCE) or a copper-copper (II) sulfate electrode (CSE). The on-chip reference electrode 912 can also comprise a pseudo-reference electrode including any metal that is not part of the active electrode such as platinum, silver, gold, or a combination thereof; any metal oxide or semiconductor oxide material such as aluminum oxide, iridium oxide, silicon oxide; or any conductive polymer electrodes such as polypyrrole, polyaniline, polyacetylene, or a combination thereof.

Each of the individual variations or embodiments described and illustrated herein has discrete components and features which may be readily separated from or combined with the features of any of the other variations or embodiments. Modifications may be made to adapt a particular situation, material, composition of matter, process, process act(s) or step(s) to the objective(s), spirit or scope of the present invention.

Methods recited herein may be carried out in any order of the recited events that is logically possible, as well as the recited order of events. For example, the flowcharts or process flows depicted in the figures do not require the particular order shown to achieve the desired result. Moreover, additional steps or operations may be provided or steps or operations may be eliminated to achieve the desired result.

It will be understood by one of ordinary skill in the art that all or a portion of the methods disclosed herein may be embodied in a non-transitory machine readable or accessible medium comprising instructions readable or executable by a processor or processing unit of a computing device or other type of machine.

Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

This disclosure is not intended to be limited to the scope of the particular forms set forth, but is intended to cover alternatives, modifications, and equivalents of the variations or embodiments described herein. Further, the scope of the disclosure fully encompasses other variations or embodiments that may become obvious to those skilled in the art in view of this disclosure. The scope of the present invention is limited only by the appended claims.

What is claimed is:

1. A method of determining a concentration of an infectious agent, the method comprising:
   diluting a sample comprising the infectious agent with a dilutive solution to yield a diluted sample;
   introducing the diluted sample to a sensor such that the diluted sample is in fluid communication with a redox-active material of the sensor, wherein the redox-active material comprises a gold layer, a platinum layer, a metal oxide layer, or a combination thereof, wherein the sensor comprises an active electrode and a reference electrode, the active electrode comprising a redox-active layer positioned on top of at least one conductive metallic layer; and
   monitoring a decrease in an oxidation reduction potential (ORP) of the diluted sample over a period of time using at least one parameter analyzer coupled to the sensor to determine the concentration of the infectious agent in the sample, wherein the ORP is monitored in the absence of any added reporter molecules in the diluted sample.

2. The method of claim 1, wherein the dilutive solution comprises growth media and the method further comprises incubating the diluted sample to between 30° C. and 40° C.

3. The method of claim 1, wherein the dilutive solution comprises at least one of deionized water and a saline solution and the method further comprises:
   introducing the diluted sample to the sensor through a sample delivery conduit comprising growth media such that the diluted sample is mixed with the growth media; and
   incubating the diluted sample mixed with the growth media to between 30° C. and 40° C.

4. The method of claim 3, wherein the growth media within the sample delivery conduit is lyophilized or dried such that the growth media mixes with the diluted sample.

5. The method of claim 3, wherein the growth media within the sample delivery conduit is in aqueous form such that the growth media mixes with the diluted sample.

6. The method of claim 1, further comprising determining the concentration of the infectious agent using a standard curve generated by monitoring the ORPs of prepared cultures of the infectious agent in different concentrations.

7. The method of claim 1, wherein the sample comprises a bodily fluid or a bacterial culture derived therefrom.

8. The method of claim 7, wherein the bodily fluid comprises urine, sputum, saliva, breast milk, spinal fluid, semen, vaginal secretions, cerebrospinal fluid, synovial fluid, pleural fluid, peritoneal fluid, pericardial fluid, amniotic fluid, cultures of bodily fluid which has been tested positive for bacteria or bacterial growth, or a combination thereof.

9. The method of claim 1, wherein diluting the sample with the dilutive solution further comprises diluting the sample to a dilution ratio between about 1:1 to about 1:10000.

10. The method of claim 1, wherein the infectious agent comprises bacteria.

11. The method of claim 7, wherein the sample is a culture of blood which has tested positive for bacteria or bacterial growth.

12. The method of claim 1, wherein the diluted sample is introduced into a container, wherein the reference electrode is an external reference electrode and extends into the diluted sample within the container from a top of the container, wherein the redox-active layer of the active electrode is in direct fluid contact with the diluted sample within the container.

13. The method of claim 1, wherein the parameter analyzer is a high-impedance voltmeter and wherein the parameter analyzer is configured to monitor the ORP of the diluted sample by measuring a relative change in an equilibrium potential at an interface between the redox-active layer of the active electrode and the diluted sample.

14. The method of claim 1, wherein monitoring the decrease in the oxidation reduction potential (ORP) of the diluted sample is performed without voltage pulses applied across the active electrode and the reference electrode.

\* \* \* \* \*